(12) United States Patent
Ballell Pages et al.

(10) Patent No.: US 10,624,893 B2
(45) Date of Patent: Apr. 21, 2020

(54) ANTITUBERCULOSIS AGENT

(71) Applicant: GlaxoSmithKline Intellectual Property Development Limited, Brentford, Middlesex (GB)

(72) Inventors: Lluis Ballell Pages, Tres Cantos (ES); David Barros Aguirre, Tres Cantos (ES); Robert H. Bates, Tres Cantos (ES); Julia Castro Pichel, Tres Cantos (ES); Jorge Esquivias Provencio, Tres Cantos (ES); Kevin Pethe, Singapore (SG)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 16/087,161

(22) PCT Filed: Mar. 20, 2017

(86) PCT No.: PCT/EP2017/056565
§ 371 (c)(1),
(2) Date: Sep. 21, 2018

(87) PCT Pub. No.: WO2017/162591
PCT Pub. Date: Sep. 28, 2017

(65) Prior Publication Data
US 2019/0091224 A1    Mar. 28, 2019

(30) Foreign Application Priority Data
Mar. 22, 2016    (EP) .................................... 16382124

(51) Int. Cl.
| A61K 31/513 | (2006.01) |
| C07D 401/06 | (2006.01) |
| A61P 31/06 | (2006.01) |
| A61K 45/06 | (2006.01) |

(52) U.S. Cl.
CPC ............ *A61K 31/513* (2013.01); *A61K 45/06* (2013.01); *A61P 31/06* (2018.01); *C07D 401/06* (2013.01)

(58) Field of Classification Search
CPC ............................ A61K 31/513; C07D 401/06
USPC .......................................... 514/274; 544/312
See application file for complete search history.

(56) References Cited

FOREIGN PATENT DOCUMENTS

EP    1 655 288 A1    5/2006

OTHER PUBLICATIONS

Database PubChem Compound [Online], "Mol Port-009-077-41511", XP002770093, Database accession No. 45833762, 11 pages (2010).

*Primary Examiner* — Jeffrey H Murray
(74) *Attorney, Agent, or Firm* — Jane F. Djung; Duke M. Fitch; Edward R. Gimmi

(57) ABSTRACT

The present invention relates to the use in therapy of 6-((4-(2,3-dimethylphenoxy)piperidin-1-yl)methyl)pyrimidine-2,4(1H,3H)-dione or a pharmaceutically acceptable salt thereof, to pharmaceutically acceptable salts of 6-((4-(2,3-dimethylphenoxy)piperidin-1-yl)methyl)pyrimidine-2,4 (1H,3H)-dione and to pharmaceutical formulations comprising 6-((4-(2,3-dimethylphenoxy)piperidin-1-yl)methyl) pyrimidine-2,4(1H,3H)-dione or a pharmaceutically acceptable salt thereof.

20 Claims, No Drawings

ANTITUBERCULOSIS AGENT

This application is a § 371 application of International Application No. PCT/EP2017/056565, filed 20 Mar. 2017, which claims priority to EP Application No. 16382124.2, filed 22 Mar. 2016, both of which are incorporated herein in their entireties.

FIELD OF THE INVENTION

This invention relates to the use in therapy of 6-((4-(2,3-dimethylphenoxy)piperidin-1-yl)methyl)pyrimidine-2,4(1H,3H)-dione or a pharmaceutically acceptable salt thereof, including use as an anti-mycobacterial, for example in the treatment of tuberculosis; compositions containing 6-((4-(2,3-dimethylphenoxy)piperidin-1-yl)methyl)pyrimidine-2,4(1H,3H)-dione or a pharmaceutically acceptable salt thereof; combinations comprising 6-((4-(2,3-dimethylphenoxy)piperidin-1-yl)methyl)pyrimidine-2,4(1H,3H)-dione. or a pharmaceutically acceptable salt thereof and salts of 6-((4-(2,3-dimethylphenoxy)piperidin-1-yl)methyl)pyrimidine-2,4(1H,3H)-dione.

BACKGROUND TO THE INVENTION

*Mycobacterium* is a genus in the class of bacteria called Actinobacteria with its own distinct family known as Mycobacteriacae. *Mycobacterium* contains various obligate and opportunistic pathogens of animals, which may also be transmitted to humans and cause disease in humans, thus exhibiting a considerable zoonotic potential. During the past few decades, members of the *Mycobacterium avium-intracellulare* complex (MAIC) emerged as pathogens of human diseases, including lymphadenitis in children, pulmonary tuberculosis-like disease, and disseminated infections (occurring predominantly in immunocompromised persons, particularly AIDS patients). Similarly, important animal diseases result from infections in an animal by members of this group, e.g., avian tuberculosis and *paratuberculosis* in ruminants. MAIC includes *M. intracellulare* and 4 subspecies of *M. avium*, namely, *M. avium* subsp. *avium, M. avium* subsp. *hominissuis, M. avium* subsp. *silvaticum*, and *M. avium* subsp. *paratuberculosis*. Whereas members of the *M. tuberculosis* complex are transmitted by direct host contact, MAIC species are acquired predominantly from environmental sources, including soil, water, dust, and feed.

*Mycobacterium tuberculosis* (MTB) is a small aerobic non-motile high-GC *bacillus* with an "outer-membrane" that is unusually thick, "waxy," hydrophobic, rich in mycolic acids, and extremely impermeable, making *mycobacterium* infections difficult to treat. One third of the world's population is thought to be infected (including latent MTB), but this number increases to upwards of 80% of the population in many Asian and African countries. If untreated, the death rate from active MTB infections is more than 50%. In addition, the combination of HIV and MTB is deadly and increasing numbers of MTB strains are becoming resistant to standard of care drugs; approximately 300,000 new cases of multidrug resistant (MDR) *M. tuberculosis* are reported each year. Multidrug resistant (MDR) *M. tuberculosis* are resistant to isoniazid and rifampicin, and extensive drug resistant (XDR) *M. tuberculosis* are also resistant to at least one quinolone and one aminoglycoside. XDR *M. tuberculosis* has been reported across much of the globe.

Add to these issues the ease of transmission, the globalization of travel, and the ongoing relocation and emigration of many segments of the world's population and it is apparent that MTB is becoming a global crisis.

Synthetic drugs for treating tuberculosis (TB) have been available for over half a century, but incidences of the disease continue to rise world-wide. More than 2 billion people are currently infected with *M. tuberculosis*, most being latent cases, and it is estimated that over 9 million new cases occur each year, worldwide, resulting in from 1.7 to nearly 2 million deaths per year. In 2004 alone approximately 24,500 new infections and close to 5,500 deaths were recorded, each day. See Zignol, Met al., M. Surveillance of anti-tuberculosis drug resistance in the world: an updated analysis, 2007-2010. Bull. World Health Organ 2012, 90 (2), 111-119D) Co-infection with HIV is driving the increase in incidence (Williams, B. G.; Dye, C. *Science*, 2003, 301, 1535) and the cause of death in 31% of AIDS patients in Africa can be attributed to TB. See Corbett, E. L et al., *Arch. Intl. Med.*, 2003, 163, 1009, Septkowitz, A et al., *Clin. Microbiol. Rev.* 1995, 8, 180).

The limitations of tuberculosis therapy and prevention are well known. The current available vaccine, BCG was introduced in 1921 and fails to protect most people past childhood. According to a 2006 report—"International Standards for Tuberculosis Care", a document developed by the Tuberculosis Coalition for Technical Assistance (TBCTA) which partners include Centers for Disease Control, American Thoracic Society, Tuberculosis Foundation, KNCV, the World Health Organization and the International Union Against Tuberculosis and Lung Disease—patients who do become infected with active disease currently endure two months of combination therapy with medicines introduced between 50 and 60 years ago—isoniazid (1952), rifampin (1963), pyrazinamide (1954) and ethambutol (1961)—followed by another 4 months of isoniazid and rifampin (also known as rifampicin). Alternatively the continuation phase could include Isoniazid and ethambutol for six months when adherence cannot be assessed, but according to this report, a longer continuation phase is associated with a higher rate of failure and relapse, especially in patients with HIV infection. Moreover, as detailed in this report, the doses of antituberculosis drugs used should conform to international recommendation and fixed-dose combinations of two (isoniazid and rifampicin), three (isoniazid, rifampicin, and pyrazinamide), and four (isoniazid, rifampicin, pyrazinamide, and ethambutol) drugs are highly recommended, especially when it is not possible to monitor the patient to ensure the treatment is ingested.

Daily dosing is required in these treatment phases and poor compliance drives the emergence and spread of multidrug-resistant strains, which are challenging to treat. Shorter courses of more active agents which can be taken less frequently and which present a high barrier to the emergence of resistance, i.e. agents which are effective against multidrug resistant strains of TB (MDR-TB), are urgently required. A March 2013 report (http://www.aidsmap.com/Once-weekly-continuation-phase-TB-treatment-equals-standard-of-care/page/2589498/) suggests that a two-drug combination of rifapentine (a long-acting derivative of rifampicin) with moxifloxacin (a fluoroquinolone antibiotic that has not been used previously in TB treatment) can allow tuberculosis (TB) treatment to be taken once-weekly during the four-month continuation phase and achieves the same standard of care as the traditional continuation treatment of daily treatment with isoniazid and rifampin. Such a treatment phase would allow treatment supervision to extend throughout the continuation phase, increasing adherence. However, moxifloxacin is not yet approved for treatment of TB, and the once-weekly treatment protocol is not yet endorsed or approved as an alternative standard of care treatment—guideline panels at international and national levels will need to review the published evidence to determine if this alternative continuation treatment protocol should be recommended and adopted. In addition, rifapentine is expensive, and interactions between rifapentine and antiretroviral drugs in the non-nucleoside reverse transcriptase inhibitor (NNRTI) and protease inhibitor classes may prevent its use in TB patients who are also HIV positive and taking antiretroviral medicines. Thus, at present, the costs/benefits analysis of a continuation treatment with weekly rifapentine versus daily rifampicin is yet to be fully assessed.

The tuberculosis drug Sirturo™ (bedaquiline) was approved in the United States in late December 2012 and is also now approved in the EU. Another tuberculosis drug, delamanid, has also gained regulatory approval in the EU as Deltyba™. However, both are reserved for drug-resistant tuberculosis, which accounts for just 5% of new cases. A 2007 Editorial and News Focus in Nature Medicine discusses many aspects of TB such as pathogenesis, epidemiology, drug discovery and vaccine development to date (*Nature Medicine*, 2007, *Focus on Tuberculosis*, Vol 13(3), pages 263-312), noting that 125 years after the anniversary of the discovery of *Mycobacterium tuberculosis*, more than one-third of people in the world are infected with *M. tuberculosis*, and of these, more than 1 in 10 will develop the disease known as tuberculosis, formerly known as consumption, in their lifetime.

When coupled with the emergence of multidrug resistant strains of *Mycobacterium tuberculosis* (MDR-TB), the scale of the problem is amplified. The global rise of bacteria and other microorganisms resistant to antibiotics and antimicrobials in general, poses a major threat. Deployment of massive quantities of antimicrobial agents into the ecosphere during the past 60 years has introduced a powerful selective pressure for the emergence and spread of antimicrobial-resistant pathogens. There is therefore a need to discover and develop new chemical entities to treat TB (recent leads are reviewed in: Grosset J H, Singer T G, Bishai W R. New Drugs for the Treatment of Tuberculosis: Hope and Reality. *Int J Tuberc Lung Dis*. 2012 August; 16(8):1005-14).

The present invention relates to the use of 6-((4-(2,3-dimethylphenoxy)piperidin-1-yl)methyl)pyrimidine-2,4 (1H,3H)-dione in therapy, and particular its unexpected activity against *Mycobacterium tuberculosis*.

SUMMARY OF THE INVENTION

In a first aspect of the invention, there is provided 6-((4-(2,3-dimethylphenoxy)piperidin-1-yl)methyl)pyrimidine-2,4(1H,3H)-dione, or a pharmaceutically acceptable salt thereof, for use in therapy.

In a second aspect of the invention there is provided a method for the treatment of a disease resulting from a mycobacterial infection in a mammal in need thereof, comprising administering to said mammal a therapeutically effective amount of 6-((4-(2,3-dimethylphenoxy)piperidin-1-yl)methyl)pyrimidine-2,4(1H,3H)-dione, or a pharmaceutically acceptable salt thereof.

In a third aspect of the invention there is provided a method for the treatment of a mycobacterial infection in a mammal in need thereof, which method comprises administering to said mammal a therapeutically effective amount of 6-((4-(2,3-dimethylphenoxy)piperidin-1-yl)methyl)pyrimidine-2,4(1H,3H)-dione, or a pharmaceutically acceptable salt thereof.

In a fourth aspect of the invention there is provided 6-((4-(2,3-dimethylphenoxy)piperidin-1-yl)methyl)pyrimidine-2,4(1H,3H)-dione, or a pharmaceutically acceptable salt thereof, for use in the treatment of a disease resulting from a mycobacterial infection in a mammal.

In a fifth aspect of the invention there is provided 6-((4-(2,3-dimethylphenoxy)piperidin-1-yl)methyl)pyrimidine-2,4(1H,3H)-dione, or a pharmaceutically acceptable salt thereof, for use in the treatment of a mycobacterial infection in a mammal.

In a sixth aspect of the invention there is provided the use of 6-((4-(2,3-dimethylphenoxy)piperidin-1-yl)methyl)pyrimidine-2,4(1H,3H)-dione, or a pharmaceutically acceptable salt thereof, in the manufacture of a medicament for use in the treatment of a mycobacterial infection in an mammal, In a seventh aspect of the invention there is provided a salt of 6-((4-(2,3-dimethylphenoxy)piperidin-1-yl)methyl)pyrimidine-2,4(1H,3H)-dione.

In an eighth aspect of the invention there is provided a pharmaceutically acceptable salt of 6-((4-(2,3-dimethylphenoxy)piperidin-1-yl)methyl)pyrimidine-2,4(1H,3H)-dione.

In a ninth aspect of the invention there is provided a combination of
a) 6-((4-(2,3-dimethylphenoxy)piperidin-1-yl)methyl)pyrimidine-2,4(1H,3H)-dione, or a pharmaceutically acceptable salt thereof; and
b) a second therapeutic agent.

In a tenth aspect of the invention there is provided a pharmaceutical composition comprising a) 6-((4-(2,3-dimethylphenoxy)piperidin-1-yl)methyl)pyrimidine-2,4(1H,3H)-dione, or a pharmaceutically acceptable salt thereof; and b) a pharmaceutically acceptable excipient.

In an eleventh aspect of the invention there is provided a method of killing a *mycobacterium* and/or inhibiting the replication of a *mycobacterium* in a mammal infected with a *mycobacterium*, comprising contacting the *mycobacterium* or treating the mammal infected with the *mycobacterium*, with a therapeutically effective amount of 6-((4-(2,3-dimethylphenoxy)piperidin-1-yl)methyl)pyrimidine-2,4(1H,3H)-dione, or a pharmaceutically acceptable salt thereof, so as to kill the *mycobacterium* and/or prevent the replication of the *mycobacterium*.

DETAILED DESCRIPTION OF THE INVENTION

The present inventors have found that 6-((4-(2,3-dimethylphenoxy)piperidin-1-yl)methyl)pyrimidine-2,4(1H,3H)-dione as described herein shows activity profiles in the assays described herein that suggest a novel mode of action. This new biological profile suggests that 6-((4-(2,3-dimethylphenoxy)piperidin-1-yl)methyl)pyrimidine-2,4(1H,3H)-dione is particularly suitable for use in combination with current anti-tubercular compounds and are envisioned to achieve greater efficacy in treating animals, including humans, infected with *M. tuberculosis*.

Resistance remains an issue in the treatment of tuberculosis (TB) and one clinical strategy is to focus on early combination with other TB drugs and to expedite early assessment of the compound's efficacy in patients. 6-((4-(2,3-dimethylphenoxy)piperidin-1-yl)methyl)pyrimidine-2,4(1H,3H)-dione offers a unique opportunity to address the serious issues which arise during the treatment of TB, such as multidrug resistance, extensive-drug resistance, reactivity and/or adverse interaction between therapeutic agents in a multidrug combination, and treatment length, thereby addressing potential patient needs.

The present invention provides 6-((4-(2,3-dimethylphenoxy)piperidin-1-yl)methyl)pyrimidine-2,4(1H,3H)-dione, that is to say the compound (I), or a pharmaceutically acceptable salt thereof, for use in therapy.

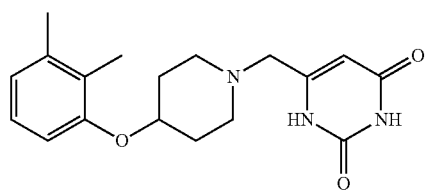

(I)

In one embodiment, in respect of the herein described method for the treatment of a disease resulting from a mycobacterial infection in a mammal in need thereof; or the herein described method for the treatment of a mycobacterial infection in a mammal in need thereof; the mammal is a human.

Another embodiment of the invention provides in respect of the herein described method for the treatment of a disease resulting from a mycobacterial infection in a mammal in need thereof; or the herein described method for the treatment of a mycobacterial infection in a mammal in need thereof; the mycobacterial infection is an infection of a *mycobacterium* selected from list A: *Mycobacterium tuberculosis, Mycobacterium avium* including subspecies (subsp.) *Mycobacterium avium* subsp. *avium, Mycobacterium avium* subsp. *hominissuis, Mycobacterium avium* subsp. *silvaticum,* and *Mycobacterium avium* subsp. *paratuberculosis, Mycobacterium kansasii, Mycobacterium malmoense, Mycobacterium simiae, Mycobacterium szulgai Mycobacterium xenopi, Mycobacterium scrofulaceum, Mycobacterium abscessus, Mycobacterium chelonae, Mycobacterium haemophilum, Mycobacterium leprae, Mycobacterium marinum, Mycobacterium fortuitum, Mycobacterium parafortuitum, Mycobacterium gordonae, Mycobacterium vaccae, Mycobacterium bovis, Mycobacterium bovis* BCG, *Mycobacterium africanum, Mycobacterium canetti, Mycobacterium caprae, Mycobacterium microti, Mycobacterium pinnipedi, Mycobacterium ulcerans, Mycobacterium intracellulare, Mycobacterium tuberculosis* complex. (MTC), *Mycobacterium avium* complex (MAC), *Mycobacterium* avian-*intracellulare* complex (MAIC), *Mycobacterium gordonae* clade; *Mycobacterium kansasii* clade; *Mycobacterium chelonae* clade; *Mycobacterium fortuitum* clade; *Mycobacterium parafortuitum* clade; and *Mycobacterium vaccae* clade.

In one embodiment, in respect of the herein described method for the treatment of a disease resulting from a mycobacterial infection in a mammal in need thereof; or the herein described method for the treatment of a mycobacterial infection in a mammal in need thereof; the mycobacterial infection is a *Mycobacterium tuberculosis* infection.

In another embodiment, in respect of the herein described method for the treatment of a disease resulting from a mycobacterial infection in a mammal in need thereof; or the herein described method for the treatment of a mycobacterial infection in a mammal in need thereof; the mycobacterial infection is an infection of a *mycobacterium* which can use cholesterol as a carbon source.

Another embodiment provides a method of treating a disease resulting from a mycobacterial infection in an animal, particularly in a mammal, more particularly in a human, which method comprises administering to the animal in need of such treatment an effective amount of 6-((4-(2,3-dimethylphenoxy)piperidin-1-yl)methyl)pyrimidine-2,4(1H,3H)-dione or a pharmaceutically acceptable salt thereof.

Another embodiment provides, in respect of the herein described method for the treatment of a disease resulting from a mycobacterial infection in a mammal in need thereof, the disease resulting from a mycobacterial infection in a mammal is selected from list B: tuberculosis, leprosy, Johne's disease, Buruli or Bairnsdale ulcer, Crohn's disease, pulmonary disease or pulmonary infection, pneumonia, bursa, synovial, tendon sheaths, localized abscess, lymphadenitis, skin and soft tissue infections Lady Windermere syndrome, MAC lung disease, disseminated *Mycobacterium avium* complex (DMAC), disseminated *Mycobacterium avium intracellulare* complex (DMAIC), hot-tub lung, MAC mastitis, MAC pyomyositis, *Mycobacterium avium paratuberculosis*, or granuloma disease. In another embodiment, in respect of the herein described method for the treatment of a disease resulting from a mycobacterial infection in a mammal in need thereof, the disease resulting from a mycobacterial infection in a mammal is tuberculosis, Another embodiment provides a method of treating a mycobacterial infection in an animal, particularly in a mammal, which method comprises administering to the animal in need of such treatment a therapeutically effective amount of 6-((4-(2,3-dimethylphenoxy)piperidin-1-yl)methyl)pyrimidine-2,4(1H,3H)-dione, or pharmaceutically acceptable salt thereof. Another embodiment provides a method of treating a mycobacterial infection in an animal, particularly a mammal, wherein the mycobacterial infection is *Mycobacterium tuberculosis*.

Another embodiment of the invention provides a method of treating a *mycobacterium* infection in an animal comprising: administering to the animal any one of: (i) a therapeutically effective amount 6-((4-(2,3-dimethylphenoxy)piperidin-1-yl)methyl)pyrimidine-2,4(1H,3H)-dione or a pharmaceutically acceptable salt thereof; (ii) a therapeutically effective amount of a combination comprising 6-((4-(2,3-dimethylphenoxy)piperidin-1-yl)methyl)pyrimidine-2,4(1H,3H)-dione or a pharmaceutically acceptable salt thereof; or (iii) a therapeutically effective amount of 6-((4-(2,3-dimethylphenoxy)piperidin-1-yl)methyl)pyrimidine-2,4(1H,3H)-dione or a pharmaceutically acceptable salt thereof, so as to treat the *mycobacterium* infection in the animal.

Another embodiment of the invention provides a method of treating a *mycobacterium* infection in an animal comprising: administering to the animal any one of: (i) a therapeutically effective amount 6-((4-(2,3-dimethylphenoxy)piperidin-1-yl)methyl)pyrimidine-2,4(1H,3H)-dione or a pharmaceutically acceptable salt thereof; (ii) a therapeutically effective amount of a combination comprising 6-((4-(2,3-dimethylphenoxy)piperidin-1-yl)methyl)pyrimidine-2,4(1H,3H)-dione or a pharmaceutically acceptable salt thereof; or (iii) a therapeutically effective amount of a pharmaceutical formulation of 6-((4-(2,3-dimethylphenoxy)piperidin-1-yl)methyl)pyrimidine-2,4(1H,3H)-dione or a pharmaceutically acceptable salt thereof, so as to treat the *mycobacterium* infection in the animal.

In one embodiment, in respect of 6-((4-(2,3-dimethylphenoxy)piperidin-1-yl)methyl)pyrimidine-2,4(1H,3H)-dione, or a pharmaceutically acceptable salt thereof, for use in the treatment of a disease resulting from a mycobacterial infection in a mammal, or for use in the treatment of a mycobacterial infection in a mammal, the mammal is a human. In another embodiment, the mycobacterial infection is an infection of a *mycobacterium* selected from the list A described hereinabove. In another embodiment, the mycobacterial infection is a *Mycobacterium tuberculosis* infection. In another embodiment, the mycobacterial infection is an infection of a *mycobacterium* which can use cholesterol as a carbon source.

The invention further provides 6-((4-(2,3-dimethylphenoxy)piperidin-1-yl)methyl)pyrimidine-2,4(1H,3H)-dione, or a pharmaceutically acceptable salt or solvate thereof, for use in the treatment of a mycobacterial infection in an animal, particularly in a human. In related aspects, the mammal is a human wherein the mycobacterial infection is a *Mycobacterium tuberculosis* infection. In one embodiment, the human with a *Mycobacterium tuberculosis* infection is also infected with a retrovirus, including a human immunodeficiency virus.

The invention further provides 6-((4-(2,3-dimethylphenoxy)piperidin-1-yl)methyl)pyrimidine-2,4(1H,3H)-dione or a pharmaceutically acceptable salt thereof, for use in the treatment of a disease resulting from a mycobacterial infection in an animal, including a human. Another embodiment of the invention provides 6-((4-(2,3-dimethylphenoxy)piperidin-1-yl)methyl)pyrimidine-2,4(1H,3H)-dione or a pharmaceutically acceptable salt thereof, for use in the treatment of a disease resulting from a mycobacterial infection in an animal, wherein the disease is selected from tuberculosis, leprosy, Johne's disease, Buruli or Bairnsdale ulcer, Crohn's disease, pulmonary disease or pulmonary infection, pneumonia, bursa, synovial, tendon sheaths, localized abscess, lymphadenitis, skin and soft tissue infections Lady Windermere syndrome, MAC lung disease, disseminated *Mycobacterium avium* complex (DMAC), disseminated *Mycobacterium avium intracellulare* complex (DMAIC), hot-tub lung, MAC mastitis, MAC pyomyositis, *Mycobacterium avium* paratuberculosis, or granuloma, disease. In another embodiment there is provided 6-((4-(2,3-dimethylphenoxy)piperidin-1-yl)methyl)pyrimidine-2,4(1H,3H)-dione or a pharmaceutically acceptable salt thereof, for use in the treatment of a disease resulting from a mycobacterial infection in an animal, wherein the disease is tuberculosis.

In one embodiment, the human with a *Mycobacterium tuberculosis* infection is also infected with a retrovirus, including a human immunodeficiency virus.

In one embodiment, in respect of the use of 6-((4-(2,3-dimethylphenoxy)piperidin-1-yl)methyl)pyrimidine-2,4(1H,3H)-dione, or a pharmaceutically acceptable salt thereof, in the manufacture of a medicament for use in the treatment of a mycobacterial infection in a mammal, the mammal is a human. In another embodiment, the mycobacterial infection is an infection of a *mycobacterium* selected from the list A described hereinabove. In another embodiment, the mycobacterial infection is a *Mycobacterium tuberculosis* infection. In another embodiment, the mycobacterial infection is an infection of a *mycobacterium* which can use cholesterol as a carbon source. In one embodiment, the disease resulting from a mycobacterial infection in a mammal is selected from the list B described hereinabove. In another embodiment, the disease resulting from a mycobacterial infection in a mammal is tuberculosis.

Another embodiment provides the use of a 6-((4-(2,3-dimethylphenoxy)piperidin-1-yl)methyl)pyrimidine-2,4(1H,3H)-dione or a pharmaceutically acceptable salt thereof in the manufacture of a medicament for the treatment of mycobacterial infection in an animal.

In one embodiment, in respect of the combination of a) 6-((4-(2,3-dimethylphenoxy)piperidin-1-yl)methyl)pyrimidine-2,4(1H,3H)-dione, or a pharmaceutically acceptable salt thereof; and b) a second therapeutic agent, the second therapeutic agent is selected from list C: isoniazid, rifampin, pyrazinamide, ethambutol, moxifloxacin, rifapentine, clofazimine, bedaquiline (TMC207), nitroimidazo-oxazine PA-824, delamanid (OPC-67683), OPC-167832, an oxazolidinone, EMB analogue SQ109, a benzothiazinone, a dinitrobenzamide and an antiviral agent including an antiretroviral agent. In a further embodiment, the oxazolidinone is linezolid, tedizolid, radezolid, sutezolid (PNU-100480), or posizolid (AZD-5847). In a further embodiment, the second therapeutic agent is a therapeutic agent approved or recommended for the treatment of tuberculosis.

In one embodiment there is provided a combination as described wherein the antiretroviral agent is independently selected from zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, GSK1349572, GSK1265744, vicriviroc (Sch-C), Sch-D, TAK779, maraviroc, TAK449, didanosine, tenofovir, lopinavir, and darunavir.

In certain embodiments of the present invention there are provided combinations of anti-tuberculosis agents and 6-((4-(2,3-dimethylphenoxy)piperidin-1-yl)methyl)pyrimidine-2,4(1H,3H)-dione, for use in the treatment of *Mycobacterium tuberculosis* infections in animals, including humans. In particular embodiments, 6-((4-(2,3-dimethylphenoxy)piperidin-1-yl)methyl)pyrimidine-2,4(1H,3H)-dione is used, in combination with other known anti-tuberculosis agents, for treating an animal subject with a *Mycobacterium tuberculosis* infection, particularly in an animal subject that is additionally infected with a human retrovirus, in particular a human immunodeficiency virus (HIV).

In one embodiment of the invention, there is provided a combination comprising: a first therapeutic agent wherein the first therapeutic agent is 6-((4-(2,3-dimethylphenoxy)piperidin-1-yl)methyl)pyrimidine-2,4(1H,3H)-dione, or a pharmaceutically acceptable salt thereof; and a second therapeutic agent; and optionally a third therapeutic agent; optionally a fourth therapeutic agent; optionally a fifth therapeutic agent; and optionally a sixth therapeutic agent, wherein the second, and optional third, fourth, fifth or sixth therapeutic agent, is other than 6-((4-(2,3-dimethylphenoxy)piperidin-1-yl)methyl)pyrimidine-2,4(1H,3H)-dione, or a pharmaceutically acceptable salt thereof.

In one embodiment there is provided a combination as described herein, wherein the second, or optional third, fourth, fifth and sixth therapeutic agent is independently selected from isoniazid, rifampin, pyrazinamide, ethambutol, moxifloxacin, rifapentine, clofazimine, bedaquiline (TMC207), nitroimidazo-oxazine PA-824, delamanid (OPC-67683), OPC-167832, an oxazolidinone such as linezolid, tedizolid, radezolid, sutezolid (PNU-100480), or posizolid (AZD-5847), EMB analogue SQ109, a benzothiazinone, a dinitrobenzamide and an antiviral agent including an antiretroviral agent.

Another embodiment of the invention provides a combination as described wherein the second, or optional third, fourth, fifth and sixth therapeutic agent is selected from a therapeutic agent approved or recommended for the treatment of tuberculosis.

Another embodiment provides a method of treating a *mycobacterium* infection in an animal comprising: administering to the animal any one of: (i) a therapeutically effective amount of 6-((4-(2,3-dimethylphenoxy)piperidin-1-yl)methyl)pyrimidine-2,4(1H,3H)-dione or a pharmaceutically acceptable salt thereof; (ii) a therapeutically effective amount of a combination comprising 6-((4-(2,3-dimethylphenoxy)piperidin-1-yl)methyl)pyrimidine-2,4(1H,3H)-dione or a pharmaceutically acceptable salt thereof; or (iii) a therapeutically effective amount of a pharmaceutical formulation comprising 6-((4-(2,3-dimethylphenoxy)piperidin-1-yl)methyl)pyrimidine-2,4(1H,3H)-dione or a pharmaceutically acceptable salt thereof, so as to treat the *mycobacterium* infection in the animal, wherein the *mycobacterium* infection is a *M. tuberculosis* infection. In one embodiment, *mycobacterium* infection is an infection of a *mycobacterium* selected from list A as described hereinabove. In another embodiment, the *mycobacterium* infection is an infection of a *mycobacterium* which can use cholesterol as a carbon source.

As described herein, embodiments of the invention include coadministering, whether simultaneously, sequentially or in combination, a first therapeutic agent that 6-((4-(2,3-dimethylphenoxy)piperidin-1-yl)methyl)pyrimidine-2,4(1H,3H)-dione, or a pharmaceutically acceptable salt thereof, in combination with a second therapeutic agent, optionally in combination with a third therapeutic agent, optionally in combination with a fourth therapeutic agent, optionally in combination with a fifth and/or a sixth therapeutic agent, to a subject exposed to or infected with a *mycobacterium* species, including a *Mycobacterium tuberculosis* species. In certain embodiments, the first therapeutic agent is 6-((4-(2,3-dimethylphenoxy)piperidin-1-yl)methyl)pyrimidine-2,4(1H,3H)-dione or a pharmaceutically acceptable salt thereof, and the second and/or third and/or fourth therapeutic agent is an anti-tubercular agent. In certain embodiments, the *mycobacterium* species is a drug-resistant variant; in certain embodiments the *mycobacterium* species is a multidrug resistant variant.

In one embodiment, the aforementioned pharmaceutical composition comprising a) 6-((4-(2,3-dimethylphenoxy)piperidin-1-yl)methyl)pyrimidine-2,4(1H,3H)-dione, or a pharmaceutically acceptable salt thereof; and b) a pharmaceutically acceptable excipient, additionally comprises a second therapeutic agent. In another embodiment, the second therapeutic agent is selected from list C described hereinabove. In a further embodiment, the oxazolidinone of list C is linezolid, tedizolid, radezolid, sutezolid (PNU-100480), or posizolid (AZD-5847). In a further embodiment, the second therapeutic agent is a therapeutic agent approved or recommended for the treatment of tuberculosis.

In one embodiment, there is provided a pharmaceutical formulation comprising 6-((4-(2,3-dimethylphenoxy)piperidin-1-yl)methyl)pyrimidine-2,4(1H,3H)-dione, or a pharmaceutically acceptable salt thereof; and a pharmaceutically acceptable excipient, adjuvant or diluent. In one embodiment, the pharmaceutical formulation comprises a second second therapeutic agent.

In one embodiment of the present invention there is provided a pharmaceutical formulation comprising a first therapeutic agent, said first therapeutic agent being a therapeutically effective amount of 6-((4-(2,3-dimethylphenoxy)piperidin-1-yl)methyl)pyrimidine-2,4(1H,3H)-dione or a pharmaceutically acceptable salt thereof. A related embodiment provides a combination as described herein and a pharmaceutically acceptable excipient, adjuvant or diluent. In another embodiment, the pharmaceutical formulation may further comprise a second therapeutic agent.

In one embodiment there is provided a pharmaceutical formulation comprising a first therapeutic agent, said first therapeutic agent being a therapeutically effective amount of 6-((4-(2,3-dimethylphenoxy)piperidin-1-yl)methyl)pyrimidine-2,4(1H,3H)-dione or pharmaceutically acceptable salt thereof, and a pharmaceutically acceptable excipient, adjuvant or diluent.

More particularly, a pharmaceutical formulation is provided comprising a first therapeutic agent that is 6-((4-(2,3-dimethylphenoxy)piperidin-1-yl)methyl)pyrimidine-2,4 (1H,3H)-dione, or a pharmaceutically acceptable salt thereof, said first therapeutic agent being a therapeutically effective amount of 6-((4-(2,3-dimethylphenoxy)piperidin-1-yl)methyl)pyrimidine-2,4(1H,3H)-dione or pharmaceutically acceptable salt thereof, in any embodiment as described herein; a pharmaceutically acceptable excipient, adjuvant or diluent; and a second therapeutic agent that is other than 6-((4-(2,3-dimethylphenoxy)piperidin-1-yl) methyl)pyrimidine-2,4(1H,3H)-dione, or a pharmaceutically acceptable salt thereof.

In related embodiments, the pharmaceutical formulation comprises a first therapeutic agent that is 6-((4-(2,3-dimethylphenoxy)piperidin-1-yl)methyl)pyrimidine-2,4(1H,3H)-dione, or a pharmaceutically acceptable salt thereof, and optionally comprises a second therapeutic agent other than 6-((4-(2,3-dimethylphenoxy)piperidin-1-yl)methyl)pyrimidine-2,4(1H,3H)-dione, or a pharmaceutically acceptable salt thereof, and optionally comprises a third therapeutic agent, and optionally comprises a fourth therapeutic agent, and optionally comprises a fifth therapeutic agent, and optionally comprises a sixth therapeutic agent. In related embodiments, the second, third, fourth, fifth and sixth therapeutic agent is an anti-mycobacterial agent other than 6-((4-(2,3-dimethylphenoxy)piperidin-1-yl)methyl)pyrimidine-2,4(1H,3H)-dione, or a pharmaceutically acceptable salt thereof. In related embodiments, the second, third, fourth, fifth and sixth therapeutic agent is selected from isoniazid, rifampin, pyrazinamide, ethambutol, moxifloxacin, rifapentine, clofazimine, bedaquiline (TMC207), nitroimidazo-oxazine PA-824, delamanid (OPC-67683), OPC-167832, an oxazolidinone such as linezolid, tedizolid, radezolid, sutezolid (PNU-100480), and posizolid (AZD-5847), EMB analogue SQ109, a benzothiazinone, a dinitrobenzamide and an antiviral agent including an antiretroviral agent. In related embodiments, the second, third, fourth, fifth and sixth therapeutic agent is a therapeutic agent approved and/or recommended for the treatment of tuberculosis.

A related embodiment provides a pharmaceutical formulation comprising 6-((4-(2,3-dimethylphenoxy)piperidin-1-yl)methyl)pyrimidine-2,4(1H,3H)-dione, or a salt thereof, and a second therapeutic agent; and optionally a third, fourth, fifth or sixth therapeutic agent, wherein the second or optional, third, fourth, fifth or sixth therapeutic agent is an antiretroviral agent selected from of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS- 626529, 5-Helix, raltegravir, elvitegravir, GSK1349572, GSK1265744, vicriviroc (Sch-C), Sch-D, TAK779, maraviroc, TAK449, didanosine, tenofovir, lopinavir, or darunavir.

In one embodiment, in respect of the method of killing a *mycobacterium* and/or inhibiting the replication of a *mycobacterium* in a mammal infected with a *mycobacterium*, comprising contacting the *mycobacterium* or treating the mammal infected with the *mycobacterium*, with a therapeutically effective amount of 6-((4-(2,3-dimethylphenoxy)piperidin-1-yl)methyl)pyrimidine-2,4(1H,3H)-dione, or a pharmaceutically acceptable salt thereof, so as to kill the *mycobacterium* and/or prevent the replication of the *mycobacterium*, the *mycobacterium* is *Mycobacterium tuberculosis*. In another embodiment, the mammal is a human. In a further embodiment, the *mycobacterium* can use cholesterol as a carbon source.

Another embodiment provides a method of killing mycobacteria and/or inhibiting replication of mycobacteria that causes disease in an animal, comprising contacting the mycobacteria with an effective amount of 6-((4-(2,3-dimethylphenoxy)piperidin-1-yl)methyl)pyrimidine-2,4(1H, 3H)-dione or a pharmaceutically acceptable salt thereof, so as to kill the mycobacteria and/or prevent the replication of the mycobacteria.

In a further embodiment, the invention provides a method of killing mycobacteria and/or inhibiting replication of mycobactera or a method of treating a mycobacterial infection in an animal such as livestock and pets, including cattle sheep, goats, dogs and cats, or a human, including an immune-suppressed human said method comprising: contacting the mycobactera with an effective amount of 6-((4-(2,3-dimethylphenoxy)piperidin-1-yl)methyl)pyrimidine-2,4(1H,3H)-dione, thereby killing the mycobacteria and/or inhibiting replication of the mycobacteria, or said method comprising administering to the animal with the mycobacterial infection a therapeutically effective amount of a compound 6-((4-(2,3-dimethylphenoxy)piperidin-1-yl)methyl)pyrimidine-2,4(1H,3H)-dione, or a pharmaceutically acceptable salt thereof. In an exemplary embodiment, 6-((4-(2,3-dimethylphenoxy)piperidin-1-yl)methyl)pyrimidine-2,4(1H,3H)-dione is part of a pharmaceutical formulation described herein. In another exemplary embodiment, the contacting occurs under conditions which permit entry of the compound into the *mycobacterium*.

In other particular embodiments there is provided a method for killing mycobacteria comprising contacting the mycobacteria or an animal, including a human, exposed to or infected with a *mycobacterium* with a first therapeutic agent that is 6-((4-(2,3-dimethylphenoxy)piperidin-1-yl)methyl)pyrimidine-2,4(1H,3H)-dione, or a pharmaceutically acceptable salt thereof, optionally contacting the cells or subject with a second therapeutic agent, optionally contacting the cells or subject with a third therapeutic agent, optionally contacting the cells or subject with a fourth therapeutic agent, optionally contacting the cells or subject with a fifth and/or a sixth therapeutic agent, such that contacting kills mycobacteria cells. In particular embodiments, the first therapeutic agent is 6-((4-(2,3-dimethylphenoxy)piperidin-1-yl)methyl)pyrimidine-2,4(1H,3H)-dione, or a pharmaceutically acceptable salt thereof and the optional second, third, fourth, fifth and/or sixth therapeutic agent is an anti-tubercular agent or a salt thereof. In other particular embodiments, the subject was exposed to or is infected with *Mycobacterium tuberculosis*.

Still other particular embodiments provide a method for inhibiting the replication of mycobacterial cells, the method comprising contacting the mycobacterial cells or an animal, including a human exposed to or infected with a mycobacterial cells with a first therapeutic agent that is 6-((4-(2,3-dimethylphenoxy)piperidin-1-yl)methyl)pyrimidine-2,4 (1H,3H)-dione or a salt thereof, optionally contacting the mycobacterial cells or animal with a second therapeutic agent, optionally contacting the mycobacterial cells or animal with a third therapeutic agent, optionally contacting the mycobacterial cells or animal with a fourth therapeutic agent, optionally contacting the mycobacterial cells or animal with a fifth and/or a sixth therapeutic agent, such that contacting inhibits the replication of the mycobacterial cells. In particular embodiments, the first therapeutic agent is 6-((4-(2,3-dimethylphenoxy)piperidin-1-yl)methyl)pyrimidine-2,4(1H,3H)-dione or a salt thereof and the optional second, third, fourth, fifth and/or sixth therapeutic agent is an anti-tubercular agent or a salt thereof. In other particular embodiments, the subject was exposed to or is infected with *Mycobacterium tuberculosis*.

The cholesterol-dependent mode-of-action of 6-((4-(2,3-dimethylphenoxy)piperidin-1-yl)methyl)pyrimidine-2,4 (1H,3H)-dione is of particular importance. This biological profile renders the compound unique among known anti-tubercular drugs. By targeting a novel pathway, the compound is expected to circumvent mechanisms of TB resistance present in clinical settings, thus providing a useful component to a new treatment regimen for tuberculosis. In addition, by targeting the cholesterol catabolism pathway, the compound may be able to target sub-populations of bacilli that are poorly sensitive to standard drugs. Thus, this compound could also have activity against other bacteria that are able to degrade cholesterol and use it as a carbon source.

DETAILED DESCRIPTION OF SPECIFIC EMBODIMENTS

"Animal" as used herein means any of a kingdom (Animalia) living organisms which feeds on organic matter, typically having specialized sense organs and nervous system and able to respond rapidly to stimuli. "Animal" includes livestock and pets, including cattle, sheep, goats, dogs and cats, or a human, including an immune-suppressed human.

"Mammal" as used herein means a warm-blooded vertebrate animal of a class that is distinguished by the possession of hair or fur, females that secrete milk for the nourishment of the young, and (typically) the birth of live young.

"Compound of the invention" as used herein refers to 6-((4-(2,3-dimethylphenoxy)piperidin-1-yl)methyl)pyrimidine-2,4(1H,3H)-dione, or a pharmaceutically acceptable salt thereof.

"Combination(s) of the invention," as used herein refers to the combination of 6-((4-(2,3-dimethylphenoxy)piperidin-1-yl)methyl)pyrimidine-2,4(1H,3H)-dione, or a pharmaceutically acceptable salt thereof; and a second therapeutic agent; and optionally a third therapeutic agent; optionally a fourth therapeutic agent; optionally a fifth therapeutic agent; and optionally a sixth therapeutic agent.

"Effective" amount of a compound, combination thereof or formulation thereof, means an amount of a compound that is the active agent, including a combination of formulation thereof, such that the amount is sufficient to provide the desired local or systemic effect. A "therapeutically effective" or "pharmaceutically effective" amount refers to the amount of compound, including a combination or formulation thereof, sufficient to achieve a desired therapeutic or pharmaceutical result.

In one aspect, the invention is directed to a salt of 6-((4-(2,3-dimethylphenoxy)piperidin-1-yl)methyl)pyrimidine-2,4(1H,3H)-dione, for example the trifluoroacetic acid salt. In a further aspect, the invention is directed to a pharmaceutically acceptable salt of a compound of 6-((4-(2,3-dimethylphenoxy)piperidin-1-yl)methyl)pyrimidine-2,4(1H,3H)-dione.

The term "pharmaceutically acceptable salt" is meant to include a salt of 6-((4-(2,3-dimethylphenoxy)piperidin-1-yl)methyl)pyrimidine-2,4(1H,3H)-dione which is prepared with relatively nontoxic acids or bases. Base addition salts can be obtained by contacting the neutral form of the compound with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, I-arginine, d-lysine or I-lysine), or magnesium salt, or a similar salt. Acid addition salts can be obtained by contacting the neutral form of the compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)).

In one embodiment of the invention, the pharmaceutically acceptable salt is selected from a hydrochloride, a hydrobromide, a hydriodide, a nitride, a carbonate, a monohydrogencarbonate, a phosphate, a monohydrogenphosphate, a dihydrogenphosphate, a sulfate, a monohydrogensulfate, a dihydrogensulfate, or a phosphonate salt.

In one embodiment of the invention, the pharmaceutically acceptable salt is selected from an acetate, a propionate, an isobutyrate, a maleate, a malonate, a benzoate, a succinate, a suberate, a fumarate, a glucaronate, a galacturonate, a lactate, a mandelate, a phthalate, a benzenesulfonate, a p-tolylsulfonate, a citrate, a tartrate, or a methanesulfonate salt.

The compound 6-((4-(2,3-dimethylphenoxy)piperidin-1-yl)methyl)pyrimidine-2,4(1H,3H)-dione contains both basic and acidic functionalities that allow the compound to be converted into either base or acid addition salts.

The neutral form of 6-((4-(2,3-dimethylphenoxy)piperidin-1-yl)methyl)pyrimidine-2,4(1H,3H)-dione is preferably regenerated by contacting the salt with a base or acid and isolating the parent compound in the conventional manner. The parent form of the compound differs from the various salt forms in certain physical properties, such as solubility in polar solvents.

It will be appreciated by those skilled in the art that the compound 6-((4-(2,3-dimethylphenoxy)piperidin-1-yl)methyl)pyrimidine-2,4(1H,3H)-dione can exist in a number of different tautomeric forms. In one embodiment, the compound is in a different tautomeric form from the chemical name 6-((4-(2,3-dimethylphenoxy)piperidin-1-yl)methyl)pyrimidine-2,4(1H,3H)-dione. In addition, the compound 6-((4-(2,3-dimethylphenoxy)piperidin-1-yl)methyl)pyrimidine-2,4(1H,3H)-dione possesses amine groups and can consequently also be in the form of a zwitterion, also known as an inner salt. Therefore, in one embodiment, the compound is in a zwitterion form. A zwitterion form may be regarded by those skilled in the art as a tautomeric form. Examples of tautomers of 6-((4-(2,3-dimethylphenoxy)piperidin-1-yl)methyl)pyrimidine-2,4(1H,3H)-dione, including an example of a zwitterion, are depicted below.

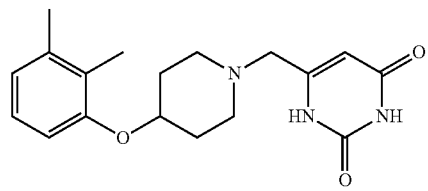

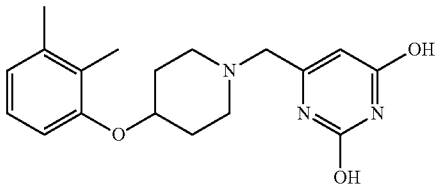

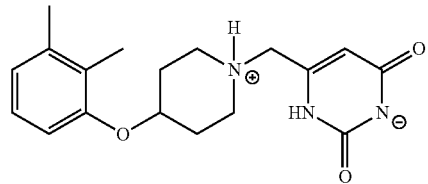

Zwitter ion

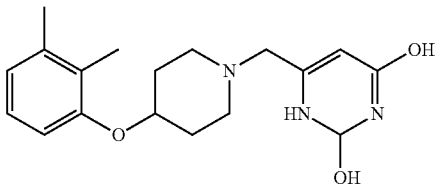

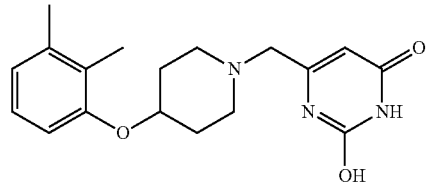

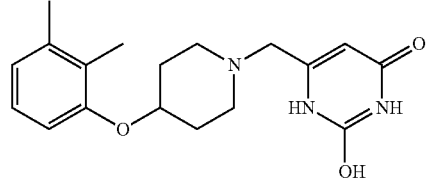

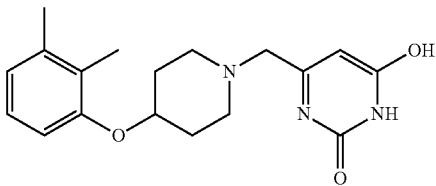

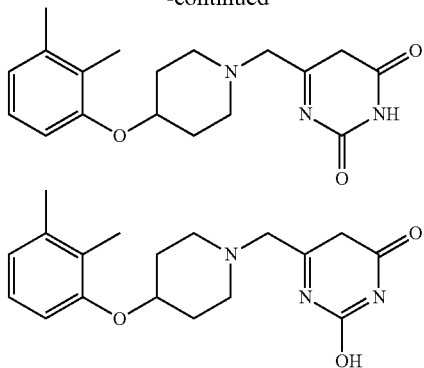

It is to be understood that reference herein to 6-((4-(2,3-dimethylphenoxy)piperidin-1-yl)methyl)pyrimidine-2,4(1H,3H)-dione is intended to encompass all tautomers thereof, and also mixtures of two or more tautomers thereof.

The compound 6-((4-(2,3-dimethylphenoxy)piperidin-1-yl)methyl)pyrimidine-2,4(1H,3H)-dione may be prepared in crystalline or non-crystalline form and, if crystalline, may optionally be solvated, e.g. as the hydrate. The solvates may be in the form of stoichiometric solvates (e.g. hydrates) as well as compound containing variable amounts of solvent (e.g. water). The The compound 6-((4-(2,3-dimethylphenoxy)piperidin-1-yl)methyl)pyrimidine-2,4(1H,3H)-dione may be prepared in isotopically-labeled forms which are identical to 6-((4-(2,3-dimethylphenoxy)piperidin-1-yl)methyl)pyrimidine-2,4(1H,3H)-dione but for the fact that one or more atoms are replaced by an atom having an atomic mass or mass number different from the atomic mass or mass number most commonly found in nature. Examples of isotopes that can be incorporated into 6-((4-(2,3-dimethylphenoxy)piperidin-1-yl)methyl)pyrimidine-2,4(1H,3H)-dione include isotopes of hydrogen, carbon, nitrogen, oxygen, fluorine, iodine and chlorine such as $^{3}$H, $^{11}$C, $^{14}$C, $^{18}$F, $^{123}$I or $^{125}$I.

Isotopically labeled compounds, for example those into which radioactive isotopes such as $^{3}$H or $^{14}$C have been incorporated, are useful in drug and/or substrate tissue distribution assays. Tritiated, ie. $^{3}$H, and carbon-14, ie. $^{14}$C, isotopes are particularly preferred for their ease of preparation and detectability. $^{11}$C and $^{18}$F isotopes are particularly useful in PET (positron emission tomography).

Because 6-((4-(2,3-dimethylphenoxy)piperidin-1-yl)methyl)pyrimidine-2,4(1H,3H)-dione as described herein is intended for use in pharmaceutical compositions it will readily be understood that it preferably provided in substantially pure form, for example at least 60% pure, more suitably at least 75% pure and preferably at least 85%, especially at least 98% pure (% are on a weight for weight basis). Impure preparations of 6-((4-(2,3-dimethylphenoxy)piperidin-1-yl)methyl)pyrimidine-2,4(1H,3H)-dione, or a salt thereof may be used for preparing the more pure forms used in the pharmaceutical compositions.

In one embodiment the invention provides a pharmaceutical composition comprising 6-((4-(2,3-dimethylphenoxy)piperidin-1-yl)methyl)pyrimidine-2,4(1H,3H)-dione, or a pharmaceutically acceptable salt thereof, and one or more pharmaceutically acceptable carriers, excipients or diluents.

Another embodiment of the invention further provides a method of treatment of a mycobacterial infection in a mammal, particularly in a human, which method comprises administering to a mammal in need of such treatment an effective amount of a first therapeutic agent that is 6-((4-(2,3-dimethylphenoxy)piperidin-1-yl)methyl)pyrimidine-2,4(1H,3H)-dione, or a pharmaceutically acceptable salt thereof. Related embodiments further comprise administering to a mammal in need of such treatment an effective amount of a first therapeutic agent that is 6-((4-(2,3-dimethylphenoxy)piperidin-1-yl)methyl)pyrimidine-2,4(1H,3H)-dione, or a pharmaceutically acceptable salt thereof, optionally administering in combination with an effective amount of a second therapeutic agent, optionally administering in combination with an effective amount of a third therapeutic agent, optionally administering in combination with an effective amount of a fourth therapeutic agent, optionally administering in combination with an effective amount of a fifth therapeutic agent, optionally administering in combination with an effective amount of a sixth therapeutic agent.

In related embodiments the optional second, third, fourth, fifth and sixth therapeutic agent is an anti-mycobacterial agent. In related embodiments, administering the first therapeutic agent and optionally administering the second, third, fourth, fifth and sixth therapeutic agent occurs concurrently, or administering the first therapeutic agent and optionally administering the second, third, fourth, fifth and sixth therapeutic agent occurs sequentially. In other related embodiments of the invention, any one of the second, third, fourth, fifth or sixth therapeutic agent is selected from an antimicrobial agent, an antiviral agent, an anti-infective agent, an analgesic, a vitamin, a nutritional supplement, an anti-inflammatory agent, an analgesic, and an steroid.

The invention also provides a pharmaceutical composition comprising 6-((4-(2,3-dimethylphenoxy)piperidin-1-yl)methyl)pyrimidine-2,4(1H,3H)-dione, or a pharmaceutically acceptable salt thereof, and one or more pharmaceutically acceptable carriers, excipients or diluents, for use in the treatment of a mycobacterial infection in a mammal, particularly in a human.

The invention also provides a pharmaceutical composition comprising 6-((4-(2,3-dimethylphenoxy)piperidin-1-yl)methyl)pyrimidine-2,4(1H,3H)-dione, or a pharmaceutically acceptable salt thereof, and one or more pharmaceutically acceptable carriers, excipients or diluents, for use in the treatment of mycobacterial infections in a mammal, particularly in a human.

In a particular embodiment, the mycobacterial infection and/or disease is treated through oral administration of the compound or combination of the invention. In an exemplary embodiment, the mycobacterial infection and/or disease is treated through intravenous administration of the compound or combination of the invention.

Pharmaceutical Formulations

In one embodiment, the invention is a pharmaceutical formulation which includes: (a) a pharmaceutically acceptable excipient; (b) a compound or combination of the invention. In another embodiment, the pharmaceutical formulation includes: (a) a pharmaceutically acceptable excipient; and (b) a compound or combination described herein. In another embodiment, the pharmaceutical formulation includes: (a) a pharmaceutically acceptable excipient; and (b) a compound or combination described herein, or a salt thereof. In another embodiment, the pharmaceutical formulation includes: (a) a pharmaceutically acceptable excipient; and (b) a compound or combination described herein, or a salt thereof. In another embodiment, the pharmaceutical formulation includes: (a) a pharmaceutically acceptable excipient; and (b) a compound or combination described herein, or a salt thereof. In another embodiment, the pharmaceutical formulation includes: (a) a pharmaceutically acceptable excipient; and (b) a salt of a compound or combination described herein. In an exemplary embodiment, the salt is a pharmaceutically acceptable salt. In another embodiment, the pharmaceutical formulation includes: (a) a pharmaceutically acceptable excipient; and (b) a compound or combination described herein. In an exemplary embodiment, the pharmaceutical formulation is a unit dosage form. In an exemplary embodiment, the pharmaceutical formulation is a single unit dosage form.

In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a three unit dosage form. In an exemplary embodiment, the pharmaceutical formulation is a four unit dosage form. In an exemplary embodiment, the pharmaceutical formulation is a five unit dosage form. In an exemplary embodiment, the pharmaceutical formulation is a six unit dosage form. In an exemplary embodiment, the pharmaceutical formulation is a one, two, three, four, five, six or seven unit dosage form comprising a first unit dosage form and a second, third, fourth, fifth and/or sixth unit dosage form, wherein the first unit dosage form includes a) a therapeutically effective amount of a compound as described herein and b) a first pharmaceutically acceptable excipient; and the second, third, fourth, fifth, and/or sixth unit dosage form includes c) a therapeutically acceptable amount of an additional therapeutic agent that is an anti-mycobacterial agent and d) a second pharmaceutically acceptable excipient.

Information regarding excipients of use in the formulations of the invention can be found in Remington: The Science and Practice of Pharmacy, 21st Ed., Pharmaceutical Press (2011) which is incorporated herein by reference.

Combinations

In an exemplary embodiment, the invention provides a) a first therapeutic agent that is 6-((4-(2,3-dimethylphenoxy)piperidin-1-yl)methyl)pyrimidine-2,4(1H,3H)-dione; b) a second therapeutic activity. In certain embodiments, the second therapeutic agent is an antibacterial agent, more specifically an anti-tubercular agent, more specifically an anti-*M. tuberculosis* agent.

In an exemplary embodiment, the combination is part of a pharmaceutical formulation described herein. Such conditions are known to one skilled in the art and specific conditions are set forth in the Examples appended hereto.

Dosage Forms of the Compound or Combinations Thereof

The individual components of the compound of the invention or combinations of the invention, for example, a combination as described herein, may be administered either simultaneously or sequentially in a unit dosage form. The unit dosage form may be a single or multiple unit dosage form. In an exemplary embodiment, the invention provides a compound or combination in a single unit dosage form. An example of a single unit dosage form is a capsule wherein the compound of the invention or both the compound of the invention and additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of the compound of the invention will be readily appreciated by those skilled in the art. Appropriate doses of an additional therapeutic agent that is other than 6-((4-(2,3-dimethylphenoxy)piperidin-1-yl)methyl)pyrimidine-2,4(1H,3H)-dione, or a pharmaceutically acceptable salt thereof, will be readily appreciated by those skilled in the art. In one particular embodiment, the compound of the invention is present alone or in the combination in a therapeutically effective amount. In one particular embodiment, the additional therapeutic agent that other than 6-((4-(2,3-dimethylphenoxy)piperidin-1-yl)methyl)pyrimidine-2,4(1H,3H)-dione is present in the combination in an amount sufficient to kill or reduce the presence, amount or growth rate of mycobacteria exposed to the compound of the invention, including *M. tuberculosis*.

The combinations of the invention, for example, a combination described herein, may also include an additional therapeutic agent or therapeutic agents. The invention thus provides, in a further embodiment, a combination comprising a compound of the invention, or a pharmaceutically acceptable salt thereof, and at least one additional therapeutic agent. The invention thus provides, in a further embodiment, a combination comprising a compound of the invention, or a pharmaceutically acceptable salt thereof, and at least one additional therapeutic agent. In an exemplary embodiment, the additional therapeutic agent is an antimycobacterial agent. In one embodiment, the invention comprises: a) a combination of the invention; and b) at least one additional therapeutic agent. In another exemplary embodiment, the invention comprises: a) a combination of the invention; b) a first additional therapeutic agent; and c) a second additional therapeutic agent. In another exemplary embodiment, the invention comprises: a) a combination of the invention; b) a first additional therapeutic agent; c) a second additional therapeutic agent; and d) a third additional therapeutic agent. The first additional therapeutic agent or second additional therapeutic agent or third additional therapeutic agent may be selected from the additional therapeutic agents described herein.

The compound of the invention or combinations may conveniently be presented for use in the form of a pharmaceutical formulation. In a further embodiment of the present invention there is provided a pharmaceutical combination comprising 6-((4-(2,3-dimethylphenoxy)piperidin-1-yl)methyl)pyrimidine-2,4(1H,3H)-dione, or a pharmaceutically acceptable salt thereof, together with one or more additional therapeutic agents, and one or more pharmaceutically acceptable carriers, excipients or diluents. The individual components of such combinations may be administered either sequentially or simultaneously in separate or combined pharmaceutical formulations by any convenient route.

When an additional therapeutic agent is used with a combination as described herein against the same disease state, the dose of each compound may differ from that when the compound is used alone. Appropriate doses will be readily appreciated by those skilled in the art. It will be appreciated that the amount of a compound as described herein required for use in treatment will vary with the nature of the condition being treated and the age and the condition of the patient and will be ultimately at the discretion of the attendant physician or veterinarian.

Composition and Formulations

The compound 6-((4-(2,3-dimethylphenoxy)piperidin-1-yl)methyl)pyrimidine-2,4(1H,3H)-dione, or a pharmaceutically acceptable salt thereof, may be formulated for administration in any convenient way for use in human or veterinary medicine, by analogy with formulation of antimycobacterial agents, or formulation of other anti-tubercular agents.

The compound 6-((4-(2,3-dimethylphenoxy)piperidin-1-yl)methyl)pyrimidine-2,4(1H,3H)-dione, or a pharmaceutically acceptable salt thereof, will normally, but not necessarily, be formulated into pharmaceutical compositions prior to administration to a patient. In one embodiment, the invention is directed to a pharmaceutical composition comprising 6-((4-(2,3-dimethylphenoxy)piperidin-1-yl)methyl)pyrimidine-2,4(1H,3H)-dione, or a pharmaceutically acceptable salt. In another embodiment the invention is directed to a pharmaceutical composition comprising 6-((4-(2,3-dimethylphenoxy)piperidin-1-yl)methyl)pyrimidine-2,4(1H,3H)-dione, or a pharmaceutically acceptable salt thereof, and one or more pharmaceutically acceptable carriers, excipients or diluents. The carrier, excipient or diluent must be "acceptable" in the sense of being compatible with the other ingredients of the formulation and not deleterious to the recipient thereof.

The pharmaceutical compositions described herein include those in a form adapted for oral or parenteral use and may be used for the treatment of a mycobacterial infection in a mammal including a human.

The pharmaceutical compositions described herein include those in a form adapted for oral or parenteral use and may be used for the treatment of mycobacterial infections in a mammal including a human.

The composition may be formulated for administration by any convenient route. For the treatment of tuberculosis, the compositions may be in the form of tablets, capsules, powders, granules, lozenges, aerosols or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 20-1000 mg of the active ingredient. The dosage as employed for adult human treatment will typically range from 50 to 300 mg per day, for instance 150 to 200 mg per day depending on the route and frequency of administration. Such a dosage corresponds to 0.5 to 5 mg/kg per day. Preferably the dosage is from 0.5 to 2 mg/kg per day and more preferably the dose is less than 1 mg/kg per day.

6-((4-(2,3-dimethylphenoxy)piperidin-1-yl)methyl)pyrimidine-2,4(1H,3H)-dione, or a pharmaceutically acceptable salt or solvate thereof, may be the sole therapeutic agent in the compositions described herein, or it may be present in the formulation in combination with one or more additional therapeutic agents. The invention thus provides, in a further embodiment, a combination comprising 6-((4-(2,3-dimethylphenoxy)piperidin-1-yl)methyl)pyrimidine-2,4(1H,3H)-dione, or a pharmaceutically acceptable salt thereof, together with one or more additional therapeutic agents.

The one or more additional therapeutic agent is, for example, an agent useful for the treatment of tuberculosis in a mammal. Examples of such therapeutic agents include, rifampin, pyrazinamide, ethambutol, moxifloxacin, rifapentine, clofazimine, bedaquiline (TMC207), nitroimidazo-oxazine PA-824, delamanid (OPC-67683), OPC-167832, an oxazolidinone such as linezolid, tedizolid, radezolid, sutezolid (PNU-100480), and posizolid (AZD-5847), EMB analogue SQ109, a benzothiazinone, a dinitrobenzamide and an antiviral agent including an antiretroviral agent, or any TB agent being developed for the treatment of TB with a positive response in Phase IIa EBA trials, or any TB agent under development by the Global Alliance for Tuberculosis.

When 6-((4-(2,3-dimethylphenoxy)piperidin-1-yl)methyl)pyrimidine-2,4(1H,3H)-dione, or a pharmaceutically acceptable salt or solvate thereof is used in combination with one or more additional therapeutic agents, the dose of the compound or agent may differ from that when the compound or agent is used alone. Appropriate doses will be readily appreciated by those skilled in the art. It will be appreciated that the amount of a compound described herein and the one or more additional therapeutic agents required for use in treatment will vary with the nature of the condition being treated and the age and the condition of the patient and will be ultimately at the discretion of the attendant physician or veterinarian.

The combinations may conveniently be presented for use in the form of a pharmaceutical formulation. In a further embodiment of the present invention there is provided a pharmaceutical combination comprising 6-((4-(2,3-dimethylphenoxy)piperidin-1-yl)methyl)pyrimidine-2,4(1H,3H)- dione, or a pharmaceutically acceptable salt thereof, together with one or more additional therapeutic agents, and one or more pharmaceutically acceptable carriers, excipients or diluents. The individual components of such combinations may be administered either sequentially or simultaneously in separate or combined pharmaceutical formulations by any convenient route.

When administration is sequential, either the compound of the present invention or one or more additional therapeutic agent may be administered first. When administration is simultaneous, the combination may be administered either in the same or different pharmaceutical composition. When combined in the same formulation it will be appreciated that the compound and agents must be stable and compatible with each other and the other components of the formulation. When formulated separately they may be provided in any convenient formulation, conveniently in such manner as are known for such compounds in the art.

Methods of Inhibiting Bacterial Growth or Killing Bacteria

The compound or combinations of the invention are expected to exhibit potency against mycobacteria and therefore have the potential to kill mycobacteria and/or inhibit the replication of mycobacteria. The compound or combinations of the invention are expected to exhibit potency against mycobacteria possessing resistance to standard-of-care anti-mycobacterial agents, and thus have the potential to kill mycobacteria and/or inhibit the replication of such "resistant" mycobacteria. In embodiments of the invention, the compound as described herein possesses significant activity against a selection of drug-sensitive mycobacterial isolates, including MDR-TB (multidrug resistant TB) clinical isolates when tested in cholesterol-containing media.

In a further embodiment, the invention provides a method of killing mycobacteria and/or inhibiting replication of mycobactera or a method of treating a mycobacterial infection in an animal such as livestock and pets, including cattle sheep, goats, dogs and cats, or a human, including an immune-suppressed human said method comprising: contacting the mycobactera with an effective amount of a compound or combination as described herein, thereby killing the mycobacteria and/or inhibiting replication of the mycobacteria, or said method comprising administering to the animal with the mycobacterial infection a therapeutically effective amount of a compound or combination of the invention, wherein the combination comprises 6-((4-(2,3-dimethylphenoxy)piperidin-1-yl)methyl)pyrimidine-2,4 (1H,3H)-dione, or a pharmaceutically acceptable salt thereof. In an exemplary embodiment, the compound or combination is part of a pharmaceutical formulation described herein. In another exemplary embodiment, the contacting occurs under conditions which permit entry of the compound or combination into the *mycobacterium*.

In an exemplary embodiment, the mycobacteria are killed or its replication is inhibited, or the mycobacterial infection is treated, through oral administration of a compound or combination as described herein. In an exemplary embodiment, the mycobacteria are killed or its replication is inhibited, or the mycobacterial infection is treated, through intravenous administration of a compound or combination as described herein. In an exemplary embodiment, the *mycobacterium* is killed or its replication is inhibited, or the mycobacterial infection is treated, through subcutaneous administration of a compound or combination as described herein, wherein the combination comprises 6-((4-(2,3-dimethylphenoxy)piperidin-1-yl)methyl)pyrimidine-2,4(1H,3H)-dione, or a pharmaceutically acceptable salt thereof.

In exemplary embodiments, the *mycobacterium* is contacted or the mycobacterial infection is treated with a combination as described herein comprising a first therapeutic agent that is 6-((4-(2,3-dimethylphenoxy)piperidin-1-yl)methyl)pyrimidine-2,4(1H,3H)-dione, or salt thereof, and a second therapeutic agent, and optionally comprising a third, fourth, fifth and sixth therapeutic agent in a population of mycobacteria comprising a resistant *mycobacterium* with a mutation conferring resistance to any one or more of the optional third, fourth, fifth and sixth therapeutic agent. In related embodiments, the optional third, fourth, fifth and sixth therapeutic agent, or a salt thereof, is an anti-mycobacterial agent, particularly a known anti-mycobacterial agent, more preferably a standard-of-care anti-mycobacterial agent.

In another exemplary embodiment, there is provided a method of killing and/or inhibiting replication of mycobacteria that causes or is associated with a disease in an animal, or a method of treating a mycobacterial infection in an animal, the method comprising contacting the mycobacteria with an effective amount of 6-((4-(2,3-dimethylphenoxy)piperidin-1-yl)methyl)pyrimidine-2,4(1H,3H)-dione or a salt thereof, so as to kill and/or prevent replication of the *mycobacterium*, or administering to the animal a therapeutically effective amount of 6-((4-(2,3-dimethylphenoxy)piperidin-1-yl)methyl)pyrimidine-2,4(1H,3H)-dione or a salt thereof, wherein the *mycobacterium* is selected from *Mycobacterium tuberculosis*, *Mycobacterium avium* including subspecies (subsp.) *Mycobacterium avium* subsp. *avium*, *Mycobacterium avium* subsp. *hominissuis*, *Mycobacterium avium* subsp. *silvaticum*, and *Mycobacterium avium* subsp. *paratuberculosis*, *Mycobacterium balnei*, *Mycobacterium sherrisii*, *Mycobacterium africanum*, *Mycobacterium microti*, *Mycobacterium silvaticum*, *Mycobacterium colombiense*, *Mycobacterium indicus pranii*, *Mycobacterium gastri*, *Mycobacterium gordonae*, *Mycobacterium hiberniae*, *Mycobacterium nonchromagenicum*, *Mycobacterium terrae*, *Mycobacterium trivial*, *Mycobacterium kansasii*; *Mycobacterium malmoense*; *Mycobacterium simiae*; *Mycobacterium triplex*, *Mycobacterium genavense*, *Mycobacterium florentinum*, *Mycobacterium lentiflavum*, *Mycobacterium palustre*, *Mycobacterium kubicae*, *Mycobacterium parascrofulaceum*, *Mycobacterium heidelbergense*, *Mycobacterium interjectum*, *Mycobacterium szulgai*, *Mycobacterium branderi* *Mycobacterium cookie*, *Mycobacterium celatum*, *Mycobacterium bohemicum*, *Mycobacterium haemophilum*, *Mycobacterium lepraemurium*, *Mycobacterium lepromatosis*, *Mycobacterium botniense*, *Mycobacterium chimaera*, *Mycobacterium conspicuum*, *Mycobacterium doricum*, *Mycobacterium forcinogenes*, *Mycobacterium heckeshornense*, *Mycobacterium lacus*, *Mycobacterium monacense*, *Mycobacterium monteforense*, *Mycobacterium murale*, *Mycobacterium nebraskense*, *Mycobacterium saskatchewanenese*, *Mycobacterium scrofulaceum*, *Mycobacterium shimoidel*, *Mycobacterium tusciae*, *Mycobacterium xenopi*, *Mycobacterium intermedium*, *Mycobacterium bolletii*, *Mycobacterium fortuitum*, *Mycobacterium foruitum* subsp. *acetamidolyticum*, *Mycobacterium boenickei*, *Mycobacterium perigrinum*, *Mycobacterium porcinum*, *Mycobacterium senegalense*, *Mycobacterium septicum*, *Mycobacterium neworleansense*, *Mycobacterium houstonense*, *Mycobacterium mucogenicum*, *Mycobacterium mageritense*, *Mycobacterium brisbanense*, *Mycobacterium cosmeticum*, *Mycobacterium parafortuitum*, *Mycobacterium austroafricanum*, *Mycobacterium diernhoferi*, *Mycobacterium hodieri*, *Mycobacterium neoaurum*, *Mycobacterium prederkisbergense*, *Mycobacterium aurum*, *Mycobacterium vaccae, *Mycobacterium chitae*, *Mycobacterium fallax*, *Mycobacterium confuentis*, *Mycobacterium flavenscens*, *Mycobacterium madagascariense*, *Mycobacterium phlei*, *Mycobacterium smegmatis*, *Mycobacterium goodie*, *Mycobacterium colinskui*, *Mycobacterium thermoresistbile*, *Mycobacterium gadium*, *Mycobacterium kormossense*, *Mycobacterium obuense*, *Mycobacterium sphagni*, *Mycobacterium agri*, *Mycobacterium aichiense*, *Mycobacterium alvei*, *Mycobacterium arupense*, *Mycobacterium brumae*, *Mycobacterium canariasense*, *Mycobacterium chubuense*, *Mycobacterium conceptionense*, *Mycobacterium duvalii*, *Mycobacterium elephantis*, *Mycobacterium gilvum*, *Mycobacterium hassiacum*, *Mycobacterium holsaticum*, *Mycobacterium immunogenum*, *Mycobacterium massiliense*, *Mycobacterium moriokaense*, *Mycobacterium psychrotoleranse*, *Mycobacterium pyrenivorans*, *Mycobacterium vanbaaleni*, *Mycobacterium pulveris*, *Mycobacterium arosiense*, *Mycobacterium aubagnense*, *Mycobacterium caprae*, *Mycobacterium chlorophenolicum*, *Mycobacterium fluoroanthenivorans*, *Mycobacterium kumamotonense*, *Mycobacterium novocastrense*, *Mycobacterium parmense*, *Mycobacterium phocaicum*, *Mycobacterium poriferae*, *Mycobacterium rhodesiae*, *Mycobacterium seolense*, *Mycobacterium tokalense*, *Mycobacterium xenopi*, *Mycobacterium scrofulaceum*; *Mycobacterium abscessus*, *Mycobacterium chelonae*; *Mycobacterium haemophilum*; *Mycobacterium leprae*, *Mycobacterium marinum*; *Mycobacterium fortuitum*; *Mycobacterium bovis*; *Mycobacterium ulcerans*; *Mycobacterium pseudoshottsii*, *Mycobacterium shottsii*, *Mycobacterium intracellulare*, *Mycobacterium tuberculosis* complex (MTC); *Mycobacterium* avian-*intracellulare* complex (MAIC) member and *Mycobacterium avium* complex (MAC) member.

In related embodiments, the *mycobacterium* is *Mycobacterium tuberculosis*. In other embodiments, the *mycobacterium* is *Mycobacterium avium*, *Mycobacterium kansasii*, *Mycobacterium malmoense*, *Mycobacterium simiae*, *Mycobacterium szulgai Mycobacterium xenopi*, *Mycobacterium scrofulaceum*, *Mycobacterium abscessus*, *Mycobacterium chelonae*, *Mycobacterium haemophilum*, *Mycobacterium leprae*, *Mycobacterium marinum*, *M. fortuitum*, *Mycobacterium bovis*, *M. bovis* BCG, *M. africanum*, *M. canetti M. caprae*, *M. microti*, *M. pinnipedi* or *Mycobacterium ulcerans*. In related embodiments, the *mycobacterium* is a subspecies (subsp.) of *Mycobacterium avium*, including *Mycobacterium avium* subsp. *avium*, *Mycobacterium avium* subsp. *hominissuis*, *Mycobacterium avium* subsp. *silvaticum*, and *Mycobacterium avium* subsp. *paratuberculosis*. In another related embodiment, the *mycobacterium* is *Mycobacterium intracellulare*. In further related embodiments, the *mycobacterium* is a member of the *Mycobacterium tuberculosis* complex. (MTC) the *Mycobacterium avium* complex (MAC) or the *Mycobacterium* avian-*intracellulare* complex (MAIC). In related embodiments, the *mycobacterium* is a non-tuberculosis complex or clade, including: *Mycobacterium avium* complex; *Mycobacterium gordonae* clade; *Mycobacterium kansasii* clade; *Mycobacterium chelonae* clade; *Mycobacterium fortuitum* clade; *Mycobacterium parafortuitum* clade, and *Mycobacterium vaccae* clade.

In an exemplary embodiment, the *mycobacterium* in the methods described herein comprises a resistant *mycobacterium*. In an exemplary embodiment, the resistant *mycobacterium* is a mutation of a *mycobacterium* described herein. In another embodiment, the mycobacterial infection is an infection of a *mycobacterium* which can use cholesterol as a carbon source.

Methods of Treating and/or Preventing Disease

The compound or combinations of the present invention exhibit potency against mycobacteria, and therefore have the potential to achieve therapeutic efficacy in animals, including humans.

In another embodiment, the invention provides a method of treating and/or preventing a disease. The method includes administering to the animal a therapeutically effective amount of a compound or combination of the invention, sufficient to treat and/or prevent the disease. In an exemplary embodiment, the compound or combination of the invention can be used in human or veterinary medical therapy, particularly in the treatment or prophylaxis of mycobacterial-associated disease.

In another exemplary embodiment, the animal is as defined herein. In another exemplary embodiment, the disease a systemic disease or a cutaneous disease. In another exemplary embodiment, the disease is a respiratory disease. In another exemplary embodiment, the disease is tuberculosis.

Compound Preparation

The general procedures which can be used to synthesise the compound 6-((4-(2,3-dimethylphenoxy)piperidin-1-yl)methyl)pyrimidine-2,4(1H,3H)-dione, and salts thereof, are summarised in reaction Scheme 1, and are illustrated in Examples 1a and 1b.

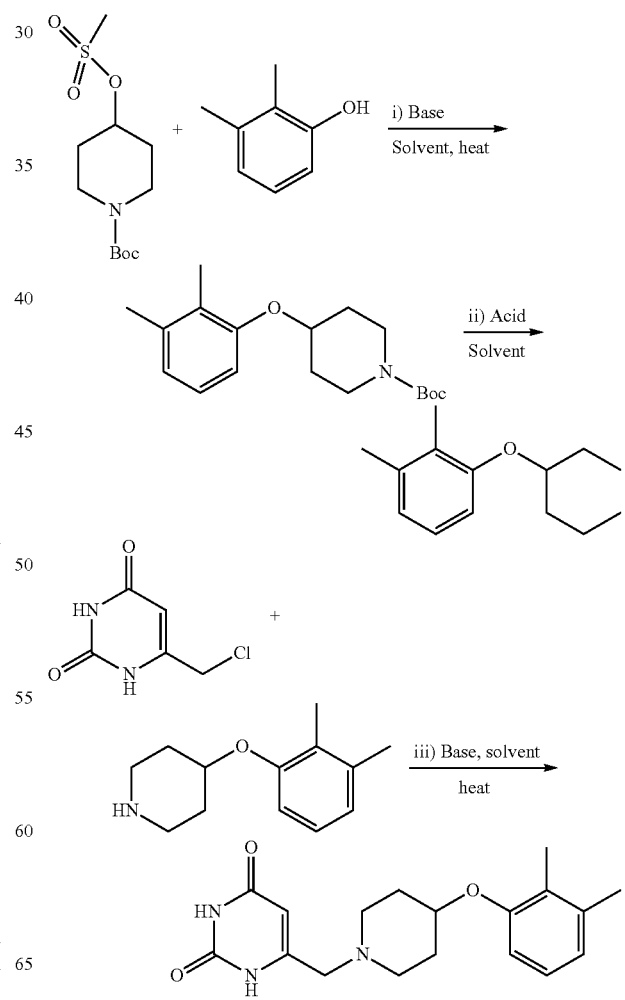

Scheme 1

-continued i) Cs$_2$CO$_3$, DMF, 90° C., 20 h; or
Cs$_2$CO$_3$, CH$_3$CN; or
Cs$_2$CO$_3$, NMP; or
Cs$_2$CO$_3$, AcNMe$_3$; or
Cs$_2$CO$_3$, DMSO; or
K$_2$CO$_3$, DMF; or
K$_2$CO$_3$, CH$_3$CN; or
K$_2$CO$_3$, NMP; or
K$_2$CO$_3$, AcNMe$_2$; or
K$_2$CO$_3$, Bu$_4$NCl, H$_2$O; or
K$_2$CO$_3$, Bu$_4$NI, DMF; or
K$_2$CO$_3$, Me$_2$CHOH; or
K$_2$CO$_3$, KI, DMF; or
K$_2$CO$_3$, K[N(SiMe$_3$)$_2$], DMF; or
K$_3$PO$_4$, DMF; or
NaH, DMF; or
tBuOH, DMSO; or
CsF, AcNMe$_2$; or
CsF, CH$_2$Cl$_2$
ii) HCl (3N), MeOH, rt, 7 h; or
HCl, Dioxane; or
HCl, AcOEt; or
HCl, H$_2$O, EtOH; or
F$_3$CCO$_2$H, CH$_2$Cl$_2$; or
AcCl, MeOH
iii) Et$_3$N, CH$_3$CN, reflux, 2 h; or
EtN(Pr-i)$_2$, CH$_3$CN;
i-Pr$_2$NH, CH$_3$CN
Et$_3$N, DMF
EtN(Pr-i)$_2$, DMF
K$_2$CO$_3$, KI, DMF; or
K$_2$CO$_3$, NaI, DMF;
K$_2$CO$_3$, NaI, BuOH
Cs$_2$CO$_3$, DMF; or;
K$_2$CO$_3$, ACNMe$_2$
EtN(Pr-i)$_2$, MeOH;
DBU, MeOH
NaOEt, DMF

ABBREVIATIONS

In describing the invention, chemical elements are identified in accordance with the Periodic Table of the Elements. Abbreviations and symbols utilized herein are in accordance with the common usage of such abbreviations and symbols by those skilled in the chemical arts. The following abbreviations are used herein:

AcOH acetic acid
Ac$_2$O acetic anhydride
ADC Albumin Dextrose Catalase
AIBN 2-2'-Azoisobutyronitrile
BOC N-tert-butoxycarbonyl
BOC anhydride di-tert-butyl dicarbonate
B$_2$pin$_2$ bis(pinacolato)diboron diboron, also known as 4,4,4',4',5,5,5',5'-octamethyl-2,2'-bi(1,3,2-dioxaborolane
Celite® a filter aid composed of acid-washed diatomaceous silica (a trademark of Manville Corp., Denver, Colo.)
CTAB cetyltrimethylammonium bromide
DCM dichloromethane
DIAD diisopropyl azodicarboxylate
DIBAL-H diisobutyl aluminium hydride
DME dimethoxyethane
DCE dichloroethane
DMF dimethylformamide
DMSO-d6 deuterated dimethylsulfoxide
DMSO dimethylsulfoxide
DS drug sensitive
ESI Electrospray ionization
ES MS Electrospray mass spectrometry
Et$_2$O diethyl ether
EtOH ethanol
EtOAc, EA ethyl acetate
h hours
HPLC high performance liquid chromatography
KOAc potassium acetate
LCMS Liquid chromatography mass spectroscopy
mCPBA meta-chloro perbenzoic acid
MDR multidrug resistant
MeNO$_2$ nitromethane
MeOH methanol
NBS N-bromosuccinimide
NCS N-chlorosuccinimide
NIS N-iodosuccinimide
NXS N-halosuccinimide
NaBH(OAc)$_3$ sodium triacetoxyborohydride
NMR Nuclear Magnetic Resonance spectroscopy
PE petroleum ether
PPh$_3$ triphenylphosphine
rt or r.t. room temperature
RT retention time
SFC supercritical fluid chromatography
t-BuOMe methyl t-butyl ether
THF tetrahydrofuran
uv ultraviolet
XDR extensively drug resistant TB

EXAMPLES

The following examples illustrate the invention. These Examples are not intended to limit the scope of the invention, but rather to provide guidance to the skilled artisan to prepare and use the compound, compositions, and methods of the invention. While particular embodiments of the invention are described, the skilled artisan will appreciate that various changes and modifications can be made. References to preparations carried out in a similar manner to, or by the general method of, other preparations, may encompass variations in routine parameters such as time, temperature, workup conditions, minor changes in reagent amounts etc.

Proton nuclear magnetic resonance ($^1$H NMR) spectra were recorded, and chemical shifts are reported in parts per million (•) relative to the solvent reference (DMSO-d6=2.50, CDCl$_3$=7.27). Abbreviations for NMR data are as follows: s=singlet, d=doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

Example 1a: Synthesis of 6-((4-(2,3-dimethylphenoxy)piperidin-1-yl)methyl)pyrimidine-2,4(1H,3H)-dione

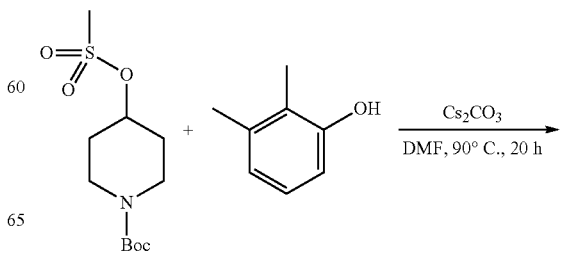

-continued

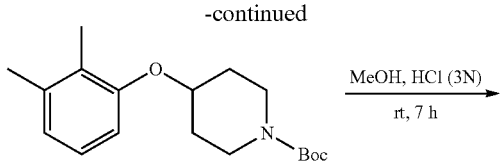

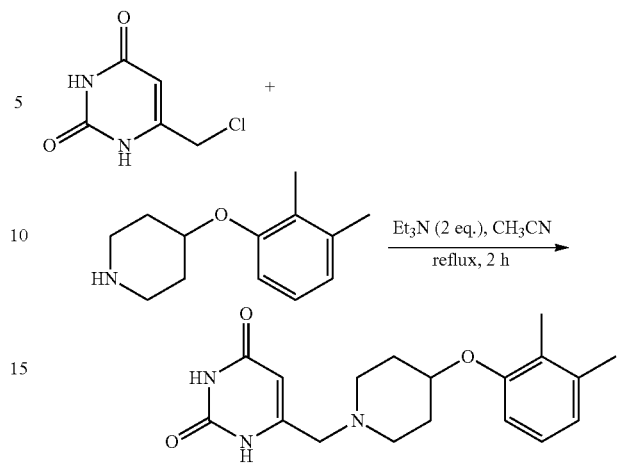

2,3-Dimethylphenol (2.14 g, 1.0 equiv.), tert-butyl 4-((methylsulfonyl)oxy)piperidine-1-carboxylate (10.04 g, 1.6 equiv.), and cesium carbonate (14.6 g, 2.0 equiv.) were dissolved in N,N-dimethyl formamide (400 mL), and the resulting solution was heated to 90° C. over 20 h. The solvent was then evaporated, and the resulting slurry was diluted with dichloromethane (250 mL) and 3M aqueous sodium hydroxide (250 mL). The aqueous layer was separated and extracted twice with dichloromethane (250 mL×2). The combined organice layers were dried over magnesium sulfate, filtered, and evaporated to afford a crude oil. This oil was partially purified by column chromatography (eluting with 0-10% ethyl acetate:cyclohexane gradient). The solvents were removed from the desired fraction by evaporation, followed by dilution again with dichloromethane (150 mL) and 3M sodium hydroxide (150 mL). The aqueous layer was separated and extracted twice with dichloromethane (2×150 mL). The combined organic layers were dried over magnesium sulfate, filtered, and evaporated to afford a ~2:1 mixture of tert-butyl 4-(2,3-dimethylphenoxy)piperidine-1-carboxylate and the elimination byproduct tert-butyl 5,6-dihydropyridine-1(2H)-carboxylate. This mixture was used directly in the next step without further purification.

The aforementioned mixture was dissolved in a 3M hydochloric acid solution in methanol (25 mL). The reaction was stirred at room temperature for 7 h until complete conversion of the starting material was observed by thin layer chromatography and NMR aliquot analysis. After evaporation of the solvents, the resulting crude solid was diluted with dichloromethane (100 mL) and 1M aqueous sodium hydroxide (100 mL). The aqueous layer was separated and extracted three times with dichloromethane (4×100 mL). The combined organic layers were dried over magnesium sulfate, filtered, and evaporated to afford a crude oil. After leaving the oil under high vacuum for 1.5 hours, trace impurities were still detected. The sample was diluted with dichloromethane (100 mL) and 2M aqueous sodium hydroxide (100 mL). The aqueous layer was separated and extracted twice with dichloromethane (2×100 mL). The combined organic layers were dried over magnesium sulfate, filtered, and evaporated to afford 4-(2,3-dimethylphenoxy)piperidine (2.93 g, quantitative yield). $^1$H NMR (400 MHz, CDCl$_3$) δ 7.03 (1H, t, J=7.8 Hz), 6.78 (1H, d, J=7.3 Hz), 6.74 (1H, d, J, =8.1 Hz), 4.35 (1H, m), 3.15 (2H, ddd, J=3.8, 6.3, 12.4 Hz), 2.74 (2H, ddd, J=3.3, 8.8, 12.4 Hz), 2.28 (3H, s), 2.18 (3H, s), 2.00 (2H, m), 1.72 (2H, m), 1.58 (1H, bs).

6-(choromethyl)pyrimidine-2,4(1H,3H)-dione (2.5 g, 1.1 equiv.), 4-(2,3-dimethylphenoxy)piperidine (2.93 g, 1.0 equiv.) and CH$_3$CN (15 mL/gr) were placed in a flask. Et$_3$N (3.95 mL, 2 equiv.) was added to the suspension and the mixture was stirred at reflux 2.5 h. Solvent was evaporated and the solids were washed with NaOH (0.5 M, 15 mL) to wash the, 6-(choromethyl)pyrimidine-2,4(1H,3H)-dione in excess, H$_2$O (3×15 mL) and Et$_2$O (2×15 mL) to give 6-((4-(2,3-dimethylphenoxy)piperidin-1-yl)methyl)pyrimidine-2,4(1H,3H)-dione with a 96% yield. $^1$H NMR (400 MHz, CD$_3$OD) δ 6.98 (1H, t, J=8.1 Hz), 6.77 (1H, d, J=8.1 Hz), 6.73 (1H, d, J=7.6 Hz), 4.49 (1H, m), 2.76 (2H, m), 2.45 (2H, m), 2.24 (3H, s), 2.15 (3H, s), 2.01 (2H, m), 1.86 (2H, m).

Example 1b: Synthesis of 6-((4-(2,3-dimethylphenoxy)piperidin-1-yl)methyl)pyrimidine-2,4(1H,3H)-dione

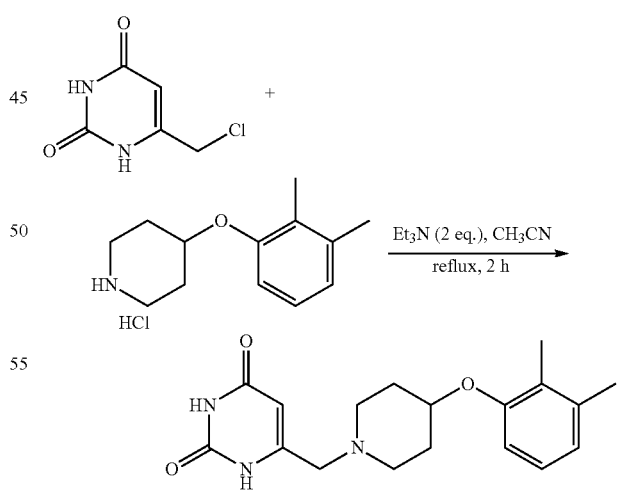

6-(chloromethyl)pyrimidine-2,4(1H,3H)-dione (166 g, 1034 mmol, 1.0 equiv) and 4-(2,3-dimethylphenoxy)piperidine, hydrochloride (250 g, 1034 mmol, 1.0 equiv) were suspended in CH$_3$CN (3 L) in a 10 L jacketed glass vessel and then triethylamine (0.288 L, 2068 mmol, 2.0 equiv) was added. The mixture was stirred at reflux for 3 h and 30 min.

Solvent was evaporated and to the crude was added NaOH (0.5 M, 1075 mL, 538 mmol, pH 9-10). The mixture was stirred for 30 min and then was filtered, washed with water (1000 mL) and dried under vacuum. The solid was dissolved in 1-butanol (1.7 L) and heated to 140° C. for 30 min and then cooled to room temperature for 3 h. The precipated was filtered off, and then suspended in $H_2O$ (2 L) and stirred to reflux for 1 h. The mixture was cooled down to 5° C. and then filtrated. The solid was washed with TBME (1000 mL) and dried under vacuum to afford 6-((4-(2,3-dimethylphenoxy)piperidin-1-yl)methyl)pyrimidine-2,4(1H,3H)-dione with a 78% yield and high purity (99.35%). $^1H$ NMR (400 MHz, DMSO-$d_6$) δ 10.94 (1H, s), 10.64 (1H, br s), 6.99 (1H, t, J=7.8 Hz), 6.81 (1H, d, J=8.1 Hz), 6.73 (1H, d, J=7.3 Hz), 5.47 (1H, s), 4.36 (1H, m), 3.20 (2H, s), 2.64 (2H, m), 2.35 (2H, m), 2.19 (3H, s), 2.08 (3H, s), 1.89 (2H, m), 1.68 (2H, m); LCMS (ES) [M+H] calculated for $C_{18}H_{23}N_3O_3$ 330.17, found 330.

The compound 6-((4-(2,3-dimethylphenoxy)piperidin-1-yl)methyl)pyrimidine-2,4(1H,3H)-dione was also purchased from Enamine.

Biological Activity

Example 2: Activity Against *Mycobacterium bovis* BCG Str. Pasteur 1173P2

The antitubercular activity against *M. bovis* BCG was done using a High Throughput Assay.

Bacterial inocula were grown for 4-5 days in Middlebrook 7H9 medium (Difco cat. #271310) with glucose as carbon source. The culture medium contained per liter: 4.7 g Middlebrook 7H9 powder, 5 g albumin, 1 g glucose, 0.85 g NaCl, and 0.25 g Tween 80. The solution was sterilized by filtration through a 0.2 µm filter.

Assay was carried out in 1536-well sterile plates (Greiner, 782074). Compound(s) to be tested was added to the plates as a 50 nL solution in neat DMSO prior to addition of the assay components by using an Echo 555 instrument (Labcyte Inc). The assay plates were subsequently filled with 5 µL of the bacterial solution (adjusted to 105 bacteria per mL) using a Multidrop Combi NL instrument (Thermo Fischer Scientific Inc.). Inoculated plates were stacked in groups of 7-8 plates, with the top plate covered with a sterile lid. Plates were carefully wrapped with aluminum foil to prevent evaporation and allowed to incubate at 37° C. at 80% relative humidity for seven days.

After the incubation period, plates were removed from the incubator and allowed to equilibrate at room temperature. Freshly reconstituted BacTiter-Glo (5 µL, Promega) was added to each well using the Multidrop Combi. After standing at room temperature for 7-8 min, the luminescence signal was quantified with an Acquest reader (Molecular Devices) in the focused luminescence mode. Every assay plate contained two columns of negative controls (ctrl 1) with DMSO, which correspond to 100% activity reactions (maximum luminescence), and two columns of positive controls (ctrl 2) in which 100% inhibition was reached by adding a known inhibitor (2 µM rifampicin as standard; bacterial growth completely inhibited). These controls were used to monitor assay quality through determination of Z' as well as for normalizing the data on a per-plate basis. The effect of a given compound is calculated as: % Inhib.=100× [(data−ctrl 1)/(ctrl 2−ctrl 1)].

|  | % Inhibition |
| --- | --- |
| Negative Control (DMSO) | 0 |
| Positive Control (Rifampicin) | 100 |
| Test Compound | 46.18 |

Example 3a: Extracellular Viability Assay (Method 1)

The antitubercular activity against *Mycobacterium tuberculosis* (H37Rv strain from ATCC cat #27294) expressing the green-fluorescent protein (GFP) growing in different carbon sources (glucose or cholesterol) was performed in 384-well plates. A starting culture was prepared by diluting a frozen aliquot in 50 mL of 7H9C medium (4.7 g/liter Middlebrook 7H9 powder, 0.81 g/liter of NaCl, 5 g/liter of BSA, 2 g/liter of d-Dextrose and 0.05% of Tween 80)

The culture was incubated for 3 days at 37° C. to obtain a growing culture with $OD_{600}$ of 0.2 to 0.3.

Standard Assay (Glucose Media)

The working inoculums were prepared by diluting the growing culture with 7H9 no glycerol media and the $OD_{600}$ was adjusted to 0.02 before adding to the assay microplate.

Cholesterol Assay (Cholesterol Media)

To prepare bacterial suspension, log-phase cells grown in 7H9 medium were used to inoculate a defined minimal medium (4.7 g/liter Middlebrook 7H9 powder, 1 g/liter $KH_2PO_4$, 2.5 g/liter $Na_2HPO_4$, 0.5 g/liter asparagine, 50 mg/liter ferric ammonium citrate, 10 mg/liter $MgSO_4.7H_2O$, 0.5 mg/liter CaCl2, and 0.1 mg/liter $ZnSO_4$, 2% of BSA, and 1 mg/ml of cholesterol) at an initial $A_{600}$ of 0.02. The cholesterol stock solution (100 mg/ml) was prepared in tyloxapol/ethanol (1:1) and warmed at 65° C. for 30 min before addition.

The test compound was serial diluted (3-fold dilution, 10 points) in 100% DMSO at a top concentration of 2 mM.

The compound master plate was replicated onto the assay plate by transferring 0.5 µL from each well using the HummingBird Plus38, 40 µl of bacterial working stock and 10 µl of medium.

The plates were incubated at 37° C. for 5 days. Bacterial growth was determined by measuring the relative fluorescence intensity using the plate reader VICTOR3. The IC50, the concentration of the compound that inhibits growth compared to the drug free control after 5 days by 50%, were determined using Graph Pad PRISM® software.

|  | IC50 (uM) (glucose media) | IC50 (uM) (cholesterol media) |
| --- | --- | --- |
| Positive Control (Rifampicin) | 0.02 | 0.04 |
| Positive Control (Isoniazid) | 0.5 | 0.2 |
| Test Compound | >20 | 0.28 |

Example 3b: Extracellular Viability Assay, Glucose Media (Method 2)

*M. tuberculosis* strain H37Rv was cultured in Middlebrook 7H9 medium supplied with 10% ADC and 0.025% Tween 80 and incubated at 37° C. for approximately 10 days.

Purity was then checked and culture was subcultured in Middlebrook 7H9 medium supplied with 10% ADC and 0.025% Tween up to OD(600 nm)=0.01 and incubated at 37°

C. for 4-6 days. The inoculum was standardized to approx. 1×107 cfu/ml by measuring the OD at 600 nm. Culture was diluted (1/100) in Middlebrook 7H9 broth supplied with 10% ADC and 0.025% Tween. 10 two-fold drug dilutions were done in DMSO into V-bottom microtitre wells and 5 ul of drug solution were added to 95 ul of Middlebrook.

7H9 medium (Row 1-10, lines A-H) was put into flat-bottom microtitre plates. In parallel, 8 two-fold dilution Isoniazid control was done in DMSO (starting at 160 ug/ml) and 5 ul of control was added to 95 ul of Middlebrook H9 medium (Row 11, lines A-H).

5 ul of DMSO were added to row 12. 100 ul of inoculum were added to the entire plate except to 12A-12F (blank controls). 100 ul of Middlebrook 7H9 medium with 10% ADC were added to blank controls. All plates were placed in a sealed box to prevent evaporation and incubate at 37° C. for six days. After that, 25 ul of resazurine solution were added to each well (one tablet in 30 ml sterile PBS) and plates were incubated at 37° C. for two additional days. Finally, fluorescence was measured. MIC value was the minimum concentration of compound giving a fluorescence signal lower than 2.5 times the average fluorescence of the blank controls. Wells could also be read visually on a microtitre mirror reader and MIC values recorded; the MIC value was considered as the minimum concentration of compound that completely inhibited visible growth of the organism as detected by the reduction of resazurin (blue wells).

|  | MIC (uM)<br>(glucose media) | MIC (uM)<br>(cholesterol media) |
| --- | --- | --- |
| Test Compound | >12.5 | ? |

Example 3c: Extracellular Viability Assay, Erdman Strain, Cholesterol Media (Method 3)

Cholesterol Medium 0.01% Preparation
Base Medium Preparation
2 bottles of 2 L of base medium were prepared:

| Ingredient | 2 liters<br>final volume |
| --- | --- |
| 0.5 g KH$_2$PO$_4$ (Panreac, Cat. #141509) | 2 g |
| 1.25 g Na$_2$HPO$_4$ (Panreac, Cat. #131679) | 5 g |
| 0.25 g L-Asparagine monohydrate (Sigma Aldrich, Cat. #A8381) | 1 g |
| 25 mg Ferric ammonium citrate (Sigma Aldrich, Cat. # 22896-6) | 100 mg |
| 5 mg MgSO$_4$•7H$_2$0 [stock 100 mg/ml] (Sigma Aldrich, Cat. #M5921) | 20 mg or 200 ul stock |
| 0.25 mg CaCl$_2$ [stock 1M] (Sigma Aldrich, Cat. #C8106)_ | 1 mg ó 18 ul stock |
| 0.05 mg ZnSO$_4$ [stock 10 mg/ml] (Sigma Aldrich, Cat. #Z2876) | 0.2 mg or 20 ul stock |

Dissolved in 449.5 ml milliQ-water.
Pre-warmed the base medium at 65° C.
Cholesterol Solution
100 mg cholesterol (Sigma, Cat.# C8667-25G) were weighed on an eppendorf tube (4 cholesterol aliquots were used per 41 medium)
A 1:1 solution of ethanol 100% (Merck Millipore, Cat.#159010) and tyloxapol 100% (Sigma, Cat. #T0307-60G) was prepared Solution was warmed up to 72° C. in a dry bath with agitation.

Cholesterol Solution:
100 mg of cholesterol were diluted in 1 ml of 1:1 tyloxapol and ethanol solution in a dry bath with agitation at 72° C. and agitated using a vortex to completely dissolve the cholesterol.

Resuspended 1 ml of cholesterol solution in 1 liter of base medium pre-warmed at 65° C.

Stirred and boiled the medium until cholesterol was completely dissolved.

Resazurin
Added 1 tablet of resazurin (Fisher Scientifics, cat #R/0040/74) per 30 ml of PBS 1×.

Cell Culture Preparation.

*Mycobacterium tuberculosis* Erdman strain was grown in base media supplemented with 0.01% cholesterol for 12-16 days until reaching an optical density [OD(600 nm)] between 0.15-0.26. Cells were diluted in fresh cholesterol medium to an initial OD(600 nm)=0.015 (1.2×10$^6$ CFU/ml) and 200 ml were dispensed per well. The plates were sealed with parafilm and incubated at 37° C. for 7 days inside a container.

After the 7 days of incubation, 25 ml of resazurin were added (see appendix section A2) to each well and incubated during 48 hours at 37° C. After that period, plates were allowed to equilibrate at room temperature and endpoint fluorescence was measured on a microplate reader Spectramax M5 spectrophotometer (Molecular Devices Equipment) at 1600 nm.

For data analysis Add-in XLFit for Excel was used to generate a non-linear regression model to fit the normalized results of the dose response curves and IC50.

|  | IC50 (uM) |
| --- | --- |
| Test Compound | 0.874 (Average over 5 measurements) |

Example 4a: Intracellular Viability Assay 1a

The antitubercular activity of the compound against *Mycobacterium tuberculosis* growing inside human THP-1 monocytes was determined using *M. tuberculosis* H37Rv containing the Firefly luciferase gene.

THP1 monocytes were maintained in suspension with RPMI-1640 media containing 10% FBS, 1 mM of Pyruvate, 2 mM of L-Glutamine, and incubated at 37° C. with 5% CO2.

Monocytes were grown to sub-confluence (5×10$^5$ cell/ml) and infected during 4 h in a cell roller bottle with a multiplicity of infection (MOI) of 1 with aseptically glass beads dispersed bacterial suspension in RPMI-0.05% Tween 80. Excess bacteria were removed by washing five times in RPMI media (1500 rpm 5 min.).

Infected cells were dispensed in 96 well white plates (50.000 cells/well) containing 1:2 serial dilutions of the compound. DMSO percentage must be below 0.5%.

Luminescence was measured after 5 days using the Steady-Glo Promega kit into a Victor 1420 system.

Results were processed by using Grafit software. IC50 values are calculated from the dose-response curves by non-linear regression analysis.

| | IC50 (uM) |
|---|---|
| Positive Control (Rifampicin) | 0.01 |
| Test Compound | 0.39 |

Example 4b: Intracellular Viability Assay 1b

The antitubercular activity of the compound against *Mycobacterium tuberculosis* growing inside human THP-1 monocytes was determined using *M. tuberculosis* H37Rv containing the Firefly luciferase gene.

THP1 monocytes were maintained in suspension with RPMI-1640 media containing 10% FBS, 1 mM of Pyruvate, 2 mM of L-Glutamine, and incubated at 37° C. with 5% CO2.

Monocytes were grown to sub-confluence ($5 \times 10^5$ cell/ml) and infected during 4 h in a cell roller bottle with a multiplicity of infection (MOI) of 1. Excess bacteria were removed by washing four times in RPMI media (1500 rpm 5 min.).

Infected cells were dispensed in 96 well white plates (50.000 cells/well) and 1:3 serial dilutions of the compound were added to the cell plate. DMSO percentage must be below 0.5%.

Luminescence was measured after 5 days using the Bright-GloPromega kit.

Results were processed by using Grafit software. MIC90 values are calculated from the dose-response curves by non-linear regression analysis.

| | IC50 (uM) |
|---|---|
| Positive Control (Rifampicin) | 0.002 |
| Test Compound | 0.07 |

Example 5: Intracellular Viability Assay 2

The antitubercular activity of the compound against *Mycobacterium tuberculosis* growing inside murine Raw 264.7 (Cat.TIB-71) cell line was determined using *M. tuberculosis* modified from the H37Rv strain obtained from ATCC (Cat. 27294) by insertion of GFP gene.

Raw macrophages cells were obtained from ATCC and cultured into macrophage culture medium (RPMIC) prepared from RPMI 1640 (Welgene, Cat. LM011-01) supplemented with 10% of Fetal Bovine Serum (Gibco, Cat. 26140-079).

A starting culture was prepared by dilution of a frozen aliquot of macrophage into 30 mL of RPMIC into a 75 cm2 cell culture flask with filtered cap. They were maintained in RPMIC at 37° C. incubator 5% CO2 and passaged by splitting 1:5 when they reached 80% confluence. They were used to quantify the intracellular activity of the compound from passage 3 but never more than passage 10.

In each experiment, rifampicin and isoniazid were tested in dose-response for quality control purposes. Rifampicin was tested from 12 μM to 0.4 nM and isoniazid from 73 μM to 2 nM (16 points dose-response curve).

The test compound was serial diluted (3-fold dilution, 10 points dilution) in 100% DMSO starting from a concentration of 2 mM (100×). Then, the compound master plates was replicated onto the assay plates, using the HummingBird Plus384, by transferring 0.5 μL into assay plates already containing 10 μL of RPMIC per well.

Macrophage cells were harvested as follow. Part of the supernatant was removed, leaving only 10 mL. Then using a cell-scrapper, the cells were gently detached, transferred to a 15 mL-conical tube and centrifuged at 1,100 rpm for 5 minutes. Supernatant was discarded and the cells were resuspended in 10 mL of fresh RPMIC. The cell number was determined using an hemocytometer.

After 2 hours infection, the cell/bacteria suspension was centrifuged at less than 1100 rpm for 5 minutes for removing extracellular bacteria. Infected cells were gently resuspended into 30 mL/tube of RPMI supplemented with only 1% FBS and centrifuged again at 1100 rpm for 5 minutes. That operation was repeated twice (total 3 washing) and the final cellular pellet resuspended with a volume of RPMIC to a cellular concentration at 300,000 cells/mL.

The assay was carried out in 384-well flat bottom microplates in a final volume of 50.5 μL. To each well containing 0.5 μL of serial diluted the test compound supplemented with 10 μl of medium, 40 μL of infected macrophages was added.

The plates were incubated at 37° C. 5% CO2 for 5 days. After 5 days, nucleus were stained by addition of 10 μL/well of Syto60 (at 30 μM giving a final concentration at 5 μM) for 1 hour at 37° C.

The plates were then transferred, to the Evotec OPERA (Perkin Elmer) fluorescence microscope equipped with Acapella acquisition software for reading with magnification of 10× Air in blue channel for Syto 60 (excitation at 635 nm reading with 690/50 filter) for nucleus/cell localization and in Green channel for GFP (Excitation at 488 nm and reading with 520/35 filter) for bacteria localization; at least 4 fields per well. Data were analyzed using Graph Pad PRISM to determine the IC50 values against *M. tuberculosis* (H37Rv-GFP).

| | IC50 (uM) |
|---|---|
| Positive Control (Rifampicin) | 0.2 |
| Positive Control (Isoniazid) | 0.07 |
| Test Compound | 0.06 |

Example 6: Acute Mouse Model

Specific pathogen-free, 8-10 week-old female C57BL/6 mice were purchased from Harlan Laboratories and were allowed to acclimate for one week. Mice were intratracheally infected with 100.000 CFU/mouse (*M. tuberculosis* H37Rv strain). The compound was administered once a day for 8 consecutive days starting one day after infection. Lungs were harvested 24 hours after the last administration. All lung lobes were aseptically removed, homogenized in distilled water and frozen. Homogenates were plated in 10% OADC-7H11 supplemented with 0.4% activated charcoal for 18 days at 37° C.

Results displayed as reduction of microorganism burden in lungs (log 10 cfu/lungs) with respect to untreated controls (Day 9):

Positive control (Moxifloxacin): 3.2 $\log_{10}$ CFU reduction at 30 mg/kg

Test compound: 1.6 $\log_{10}$ CFU reduction at 200 mg/kg

Example 7: Extracellular Assay for Multidrug Resistant (MDR) *M. tuberculosis*

*M. tuberculosis* drug resistant strains were grown to an OD of 0.2-0.6 in a regular 7H9-based medium supplemented with 97 mg/mL cholesterol in a 24-well plate. In a 96-well clear round bottom plate 50 uL of medium were added except in the first row. 100 uL of each drug diluted in the same medium were added in the first row at 100 uM. 50 uL was transferred to each well from row 1 to 12. To each well $2\times10^4$ bacteria were added and the plates were incubated for 3 weeks at 37° C. in a zip-lock bag. At various time points and inverted enlarging mirror plate reader was used to grade as either growth or no growth. MIC was established as the concentration that completely inhibited growth. MIC must be read early when growth is clearly visible to avoid outgrowth at longer time points related to resistance or regulatory adaptive mechanisms. This time-point is strain dependent (generally between 1 and 2 weeks).

At week 2, $\frac{1}{10}^{th}$ volume of Alamar Blue was added to plates with 7H9-regular and cholesterol medium. After incubation at 37° C. for 24 h the plates were read through visual scoring (blue=growth inhibition, pink=growth). Alamar Blue addition to cholesterol medium is necessary to distinguish cholesterol precipitation from growth which occurs if the media cooled down during MIC setup.

DISCUSSION

The data presented in Examples 2-7 above illustrate that 6-((4-(2,3-dimethylphenoxy)piperidin-1-yl)methyl)pyrimidine-2,4(1H,3H)-dione possesses anti-mycobacterial activity under specific conditions, namely when the bacili are inside macrophages, or otherwise in the presence of cholesterol such as in an extracellular assay with a cholesterol medium. These findings are consistent given that macrophages are known to have high intracellular cholesterol concentrations. This cholesterol-related biological profile of the compound is unusual, and suggests that the compound acts via a novel mechanism of action. Novel biological targets are desirable in TB therapy due to the expectation that pre-existing resistance is unlikely to exist in the field. Additionally, by targeting mycobacteria that can use cholesterol as a carbon source, this compound may be able contribute a unique bacteriocidal component to a TB com-

| TB Strain ID | Clinical phenotype | Resistance profile | MIC 1 (uM) | MIC 2 (uM) |
|---|---|---|---|---|
| NIH_G1DS | DS | | 0.78 | 0.39 |
| K03b00DS | DS | | 0.3 | 0.2 |
| K33b00MR | MDR | HREZSKPTh | 0.6 | 0.39 |
| K33b00MR (independent freezer stock) | MDR | HREZSKPTh | Not tested | 0.78 |
| K04b00DS | DS | | 0.39 | Not tested |
| K07b00DS | DS | | 0.6 | 0.39 |
| K08b00DS | DS | | 0.6 | 0.39 |
| K11b00DS | DS | | 1.2 | 0.78 |
| K12b00DS | DS | | 0.2 | 0.6 |
| NIH_G2XR | XDR | HREKOPZSPThCapMC | Not tested | 0.39 |
| NIH_G3XR | XDR | HRECKOPZSPThCapM | Not tested | 0.78 |
| K37b00XR | XDR | HREKOPM | 0.6 | 0.6 |
| NIH_G4XR | XDR | HREPKOTh | 1.2 | 0.6 |
| K32b00MR | MDR | HREKP | 0.6 | 0.39 |
| K21b00MR | MDR | HRES | 0.78 | 0.39 |
| NIH_G5MR | MDR | HREKO | 1.2 | 0.3 |
| NIH_G6MR | MDR | HREOPZPThM | Not tested | 0.39 |
| K29b00MR | MDR | HRSPO | 0.39 | 0.39 |
| K22b00MR | MDR | HRERb | 0.6 | 0.6 |
| K35b00DS | DS | | 0.6 | 0.39 |
| K13b00DS | DS | | 0.78 | 0.6 |
| K14b00DS | DS | | 1.2 | 0.6 |
| K16b00DS | DS | | 0.39 | 0.2 |
| K20b00MR | MDR | HREZSKP | Not tested | 0.2 |
| K25b00MR | MDR | HREZRbTh | Not tested | 0.6 |
| K26b00MR | MDR | HREZRb | 0.39 | 0.3 |
| NIH_G7XR | XDR | HREKOZMRbCapAm | Not tested | 0.6 |
| NIH_G8MR | MDR | HRPRb | Not tested | 0.39 |
| K25b00MR | MDR | HREPThRb | 0.78 | Not tested |
| NIHCRC_1 | XDR | HREMKPSEt | Not tested | 1.2 |
| NIH_G9R | | MC | Not tested | 0.6 |
| NIH_G10R | | HRESRb | Not tested 1.2 | 0.78 |
| NIH_G11R | | EC | Not tested | 1.2 |
| NIH_G12 | | | 0.78 | Not tested |
| NIH_G13 | | | 0.6 | 1.2 |
| NIH_G14 | | | 1.2 | |
| NIH_G15R | | HRCRbEt | 1.2 | 1.2 |
| NIH_G16R | | SC | 1.56 | 1.2 |
| NIH_G17R | | HCEt | 1.56 | 0.78 |
| NIH_G18R | | HRSEP | 1.2 | Not tested |
| NIH_G19R | | HRESCRb | 1.2 | 1.2 |
| NIH_G20R | | C | 1.2 | 0.39 |
| NIH_G21R | | HRERb | 0.78 | 0.6 |
| NIH_G22R | | HCS | 0.78 | 0.6 |
| CDC1551 | DS | | 0.78 | 0.39 |
| Erdman | DS | | 0.78 | 0.6 |
| HN878 | DS | | 0.78 | 0.6 |
| M. africanum | | | 1.2 | 1.2 |
| M. bovis 0AF2122 | | | Not tested | 0.78 |
| H37Rv | DS | | Not tested | 0.39 | bination drug regimen. Finally, the murine in vivo data demonstrate that 6-((4-(2,3-dimethylphenoxy)piperidin-1-yl)methyl)pyrimidine-2,4(1H,3H)-dione is orally bioavailable and efficacious against bacteria under the heterogeneic conditions found in animal experiments.

It is to be understood that the invention covers all combinations of embodiments with all other suitable embodiments and/or exemplary embodiments described herein. It is to be understood that the invention also covers all combinations of exemplary embodiments with all other suitable embodiments described herein.

It is understood that the examples and embodiments described herein are for illustrative purposes only and that various modifications or changes in light thereof will be suggested to persons skilled in the art and are to be included within the spirit and purview of this application and scope of the appended claims.

The invention claimed is:

1. A method for the treatment of a disease resulting from a mycobacterial infection in a human in need thereof, comprising administering to said human a therapeutically effective amount of 6-((4-(2,3-dimethylphenoxy)piperidin-1-yl)methyl)pyrimidine-2,4(1H,3H)-dione, or a pharmaceutically acceptable salt thereof.

2. A method for the treatment of a mycobacterial infection in a human in need thereof, the method comprising administering to said human a therapeutically effective amount of 6-((4-(2,3-dimethylphenoxy)piperidin-1-yl)methyl)pyrimidine-2,4(1H,3H)-dione, or a pharmaceutically acceptable salt thereof.

3. The method according to claim 1, wherein the mycobacterial infection is a *Mycobacterium tuberculosis* infection.

4. The method according to claim 1, wherein the disease is tuberculosis.

5. A salt of 6-((4-(2,3-dimethylphenoxy)piperidin-1-yl)methyl)pyrimidine-2,4(1H,3H)-dione.

6. A pharmaceutically acceptable salt of 6-((4-(2,3-dimethylphenoxy)piperidin-1-yl)methyl)pyrimidine-2,4(1H,3H)-dione.

7. The method according to claim 1, further comprising administering a therapeutically effective amount of a second therapeutic agent.

8. The method according to claim 7, wherein the second therapeutic agent is selected from the group consisting of isoniazid, rifampin, pyrazinamide, ethambutol, moxifloxacin, rifapentine, clofazimine, bedaquiline, nitroimidazo-oxazine PA-824, delamanid, OPC-167832, an oxazolidinone, EMB analogue SQ109, a benzothiazinone, a dinitrobenzamide, and an antiviral agent.

9. The method according to claim 8, wherein the oxazolidinone is linezolid, tedizolid, radezolid, sutezolid, or posizolid.

10. The method according to claim 7, wherein the second therapeutic agent is a therapeutic agent approved for or recommended for the treatment of tuberculosis.

11. A pharmaceutical composition comprising a) 6-((4-(2,3-dimethylphenoxy)piperidin-1-yl)methyl)pyrimidine-2,4(1H,3H)-dione, or a pharmaceutically acceptable salt thereof; and b) a pharmaceutically acceptable excipient.

12. The pharmaceutical composition according to claim 11, further comprising a second therapeutic agent.

13. The pharmaceutical composition according to claim 12, wherein the second therapeutic agent is selected from the group consisting of isoniazid, rifampin, pyrazinamide, ethambutol, moxifloxacin, rifapentine, clofazimine, bedaquiline, nitroimidazo-oxazine PA-824, delamanid, OPC-167832, an oxazolidinone, EMB analogue SQ109, a benzothiazinone, a dinitrobenzamide, and an antiviral agent.

14. A method of killing a mycobacterium and/or inhibiting the replication of a mycobacterium in a human infected with a *mycobacterium*, comprising contacting the *mycobacterium* or treating the human infected with the *mycobacterium*, with a therapeutically effective amount of 6-((4-(2,3-dimethylphenoxy)piperidin-1-yl)methyl)pyrimidine-2,4(1H,3H)-dione, or a pharmaceutically acceptable salt thereof.

15. The method according to claim 14, wherein the mycobacterium is *Mycobacterium tuberculosis*.

16. The method according to claim 2, wherein the mycobacterial infection is a *Mycobacterium tuberculosis* infection.

17. The method according to claim 8, wherein the antiviral agent is an antiretroviral agent.

18. The pharmaceutical composition according to claim 13, wherein the antiviral agent is an antiretroviral agent.

19. The pharmaceutical composition according to claim 13, wherein the oxazolidinone is linezolid, tedizolid, radezolid, sutezolid, or posizolid.

20. The pharmaceutical composition according to claim 12, wherein the second therapeutic agent is a therapeutic agent approved for or recommended for the treatment of tuberculosis.

* * * * *